United States Patent
Eggers et al.

(12) 
(10) Patent No.: US 6,416,507 B1
(45) Date of Patent: *Jul. 9, 2002

(54) METHOD FOR TREATING ARTICULAR CARTILAGE DEFECTS

(75) Inventors: Philip E. Eggers, Dublin, OH (US); Hira V. Thapliyal, Los Altos, CA (US)

(73) Assignee: ArthroCare Corporation, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/484,087

(22) Filed: Jan. 18, 2000

Related U.S. Application Data

(63) Continuation of application No. 09/177,861, filed on Oct. 23, 1998, now Pat. No. 6,066,134, which is a division of application No. 08/795,686, filed on Feb. 5, 1997, now Pat. No. 5,871,469, which is a division of application No. 08/561,958, filed on Nov. 22, 1995, now Pat. No. 5,697,882, which is a continuation-in-part of application No. 08/485,219, filed on Jun. 7, 1995, now Pat. No. 5,697,281, which is a continuation-in-part of application No. PCT/US94/05168, filed on May 10, 1994, which is a continuation-in-part of application No. 08/059,681, filed on May 10, 1993, now abandoned, which is a continuation-in-part of application No. 07/958,977, filed on Oct. 9, 1992, now Pat. No. 5,366,443, which is a continuation-in-part of application No. 07/817,575, filed on Jan. 7, 1992, now abandoned.

(51) Int. Cl.⁷ .......................... A61B 18/12; A61B 18/14
(52) U.S. Cl. .............................. 606/32; 606/41; 606/46; 604/114; 607/99; 607/105; 607/113
(58) Field of Search .................. 606/32, 41, 46, 606/49; 607/98, 99, 105, 113; 604/114

(56) References Cited

U.S. PATENT DOCUMENTS

| | | |
|---|---|---|
| 2,050,904 A | 8/1936 | Trice |
| 4,033,351 A | 7/1977 | Hetzel .......................... 128/303 |
| 4,040,426 A | 8/1977 | Morrison, Jr. .............. 128/303 |
| 4,043,342 A | 8/1977 | Morrison, Jr. .............. 128/303 |
| 4,116,198 A | 9/1978 | Roos ........................... 128/303 |
| 4,184,492 A | 1/1980 | Meinke et al. .............. 128/303 |
| 4,202,337 A | 5/1980 | Hren et al. .................. 128/303 |

(List continued on next page.)

FOREIGN PATENT DOCUMENTS

| | | | |
|---|---|---|---|
| EP | 0 703 461 A2 | 3/1996 | ........... G01R/27/02 |
| EP | 0 740 926 A2 | 11/1996 | ........... A61B/17/39 |
| EP | 0 754 437 | 1/1997 | ........... A61B/17/39 |
| GB | 2 308 979 | 7/1997 | |
| GB | 2 308 980 | 7/1997 | |
| GB | 2 308 981 | 7/1997 | |

(List continued on next page.)

OTHER PUBLICATIONS

Slager et al. (1985) *JACC* 5(6): 1382–6.
Slager et al. (1987) *Z. Kardiol.* 76:Suppl. 6, 67–71.
V.E. Elsasser et al. *Acta Medicotechnica* 24(4):129–134 (1976).

(List continued on next page.)

*Primary Examiner*—Lee Cohen
(74) *Attorney, Agent, or Firm*—John T. Raffle; Sanjay S. Bagade

(57) ABSTRACT

An electrosurgical probe (10) comprises a shaft (13) having an electrode array (58) at its distal end and a connector (19) at its proximal end for coupling the electrode array to a high frequency power supply (28). The shaft includes a return electrode (56) recessed from its distal end and enclosed within an insulating jacket (18). The return electrode defines an inner passage (83) electrically connected to both the return electrode and the electrode array for passage of an electrically conducting liquid (50). By applying high frequency voltage to the electrode array and the return electrode, the electrically conducting liquid generates a current flow path between the return electrode and the electrode array so that target tissue may be cut or ablated. The probe is particularly useful in dry environments, such as the mouth or abdominal cavity, because the electrically conducting liquid provides the necessary return current path between the active and return electrodes.

26 Claims, 18 Drawing Sheets

U.S. PATENT DOCUMENTS

| | | | |
|---|---|---|---|
| 4,228,800 A | 10/1980 | Degler, Jr. et al. | 128/303 |
| 4,232,676 A | 11/1980 | Herczog | 128/303 |
| 4,248,231 A | 2/1981 | Herczog et al. | 128/303 |
| 4,326,529 A | 4/1982 | Doss | 128/303.1 |
| 4,381,007 A | 4/1983 | Doss | 128/303.1 |
| 4,476,862 A | 10/1984 | Pao | 128/303.17 |
| 4,532,924 A | 8/1985 | Auth et al. | 128/303.17 |
| 4,548,207 A | 10/1985 | Reimels | 128/303 |
| 4,567,890 A | 2/1986 | Ohta et al. | 128/303.13 |
| 4,593,691 A | 6/1986 | Lindstrom et al. | 128/303.14 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,709,698 A | 12/1987 | Johnston et al. | 128/303 |
| 4,727,874 A | 3/1988 | Bowers et al. | 128/303 |
| 4,765,331 A | 8/1988 | Petruzzi et al. | 128/303 |
| 4,823,791 A | 4/1989 | D'Amelio et al. | 123/303 |
| 4,860,752 A | 8/1989 | Turner | 128/422 |
| 4,931,047 A | 6/1990 | Broadwin et al. | 604/22 |
| 4,936,301 A | 6/1990 | Rexroth et al. | 606/45 |
| 4,943,290 A | 7/1990 | Rexroth et al. | 606/45 |
| 4,955,377 A | 9/1990 | Lennox et al. | 128/401 |
| 4,967,765 A | 11/1990 | Turner et al. | 128/785 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 604/41 |
| 5,007,908 A | 4/1991 | Rydell | 606/47 |
| 5,009,656 A * | 4/1991 | Reimels | 606/48 |
| 5,035,696 A | 7/1991 | Reydell | 606/47 |
| 5,057,105 A | 10/1991 | Malone et al. | 606/28 |
| 5,057,106 A | 10/1991 | Kasevich et al. | 606/33 |
| 5,078,717 A | 1/1992 | Parins et al. | 606/48 |
| 5,080,660 A | 1/1992 | Buelna | 606/48 |
| 5,083,565 A | 1/1992 | Parins | 128/642 |
| 5,098,431 A | 3/1992 | Rydell | 606/48 |
| 5,108,391 A | 4/1992 | Flachenecker et al. | 606/38 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,178,620 A | 1/1993 | Eggers et al. | 606/41 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,197,963 A | 3/1993 | Parins | 606/46 |
| 5,217,457 A | 6/1993 | Delahuerga et al. | 606/42 |
| 5,249,585 A | 10/1993 | Turner et al. | 607/99 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,281,218 A | 1/1994 | Imran | 606/41 |
| 5,290,282 A | 3/1994 | Casscells | 606/29 |
| 5,300,069 A | 4/1994 | Hunsberger et al. | 606/37 |
| 5,312,400 A | 5/1994 | Bales et al. | 606/41 |
| 5,314,406 A | 5/1994 | Arias et al. | 604/21 |
| 5,318,563 A | 6/1994 | Malis et al. | 606/38 |
| 5,324,254 A | 6/1994 | Phillips | 604/21 |
| 5,330,470 A | 7/1994 | Hagen | 606/42 |
| 5,334,140 A | 8/1994 | Phillips | 604/35 |
| 5,334,183 A | 8/1994 | Wuchinich | 606/46 |
| 5,336,220 A | 8/1994 | Ryan et al. | 604/22 |
| 5,342,357 A | 8/1994 | Nardella | 606/40 |
| 5,366,443 A | 11/1994 | Eggers et al. | 604/114 |
| 5,370,675 A | 12/1994 | Edwards et al. | 607/101 |
| 5,380,277 A | 1/1995 | Phillips | 604/33 |
| 5,383,876 A | 1/1995 | Nardella | 606/49 |
| 5,383,917 A | 1/1995 | Desai et al. | 607/702 |
| 5,395,312 A | 3/1995 | Desai | 604/22 |
| 5,417,687 A | 5/1995 | Nardella et al. | 606/32 |
| 5,419,767 A | 5/1995 | Eggers et al. | 604/114 |
| 5,441,499 A | 8/1995 | Fritzsch | 606/45 |
| 5,454,809 A | 10/1995 | Janssen | 606/41 |
| 5,496,312 A | 3/1996 | Klicek | 606/34 |
| 5,514,130 A | 5/1996 | Baker | 606/41 |
| 5,556,397 A | 9/1996 | Long et al. | 606/48 |
| 5,569,242 A | 10/1996 | Lax et al. | 606/42 |
| 5,584,872 A | 12/1996 | LaFontaine et al. | 607/116 |
| 5,609,151 A | 3/1997 | Mulier et al. | 128/642 |
| 5,626,576 A * | 5/1997 | Janssen | 606/41 |
| 5,647,869 A | 7/1997 | Goble et al. | 606/37 |
| 5,676,693 A | 10/1997 | LaFontaine et al. | 607/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,700,262 A | 12/1997 | Acosta et al. | 606/48 |
| 5,725,524 A | 3/1998 | Mulier et al. | 606/41 |
| 5,749,869 A | 5/1998 | Lindenmeier et al. | 606/34 |
| 5,766,153 A | 6/1998 | Eggers et al. | 604/114 |
| 5,807,395 A | 9/1998 | Mulier et al. | 606/41 |
| 5,810,764 A | 9/1998 | Eggers et al. | 604/23 |
| 5,843,019 A | 12/1998 | Eggers et al. | 604/22 |
| 5,871,469 A | 2/1999 | Eggers et al. | 604/114 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,897,553 A | 4/1999 | Mulier | 606/41 |
| 5,944,715 A | 8/1999 | Goble et al. | 606/41 |
| 6,066,134 A * | 5/2000 | Eggers et al. | 606/32 |

FOREIGN PATENT DOCUMENTS

| | | | |
|---|---|---|---|
| JP | 57-57802 | 4/1982 | A61B/1/00 |
| JP | 57-117843 | 7/1982 | A61B/17/39 |
| WO | WO 97/07303 | 7/1990 | A61B/17/39 |
| WO | WO 92/21278 | 12/1992 | A61B/5/04 |
| WO | WO 93/13816 | 7/1993 | A61B/17/36 |
| WO | 93/20747 | 10/1993 | A61B/5/00 |
| WO | 94/04220 | 3/1994 | A61N/1/06 |
| WO | 94/08654 | 4/1994 | A61M/37/00 |
| WO | 95/32459 | 12/1995 | A61F/5/48 |
| WO | 97/00646 | 1/1997 | A61B/17/39 |
| WO | 97/00647 | 1/1997 | A61B/17/39 |
| WO | 97/24073 | 7/1997 | A61B/17/39 |
| WO | 97/24993 | 7/1997 | A61B/17/39 |
| WO | 97/24994 | 7/1997 | A61B/17/39 |
| WO | 97/48346 | 12/1997 | A61B/17/39 |
| WO | 98/07468 | 2/1998 | |
| WO | 98/27879 | 7/1998 | A61B/17/36 |
| WO | 98/27880 | 7/1998 | |
| WO | 99/51158 | 10/1999 | A61B/17/39 |

OTHER PUBLICATIONS

M. Buchelt et al. *Lasers in Surgery and Medecine* 11:271–279 (1991).

E. Kramolowsky et al. *J. of Urology* 143:275–277 (1990).

J. Costello *Lasers in Surgery and Medicine* 12:121–124 (1992).

E.V. Kramolowsky et al. *J. of Urology* vol. 143, pp. 275–277 (1990).

J.W. Ramsey et al. *Urological Research* vol. 13, pp. 99–102 (1985).

P.C. Nardella (1989) *SPIE* 1068;42–49 Radio Frequency Energy and Impedance Feedback.

R. Tucker et al., Abstract P–14–11, p. 248, "A Bipolar Electrosurgical Turp Loop".

R. Tucker et al. *J. of Urology* vol. 141, pp. 662–665, (1989).

R. Tucker et al. *Urological Research* vol. 18, pp. 291–294 (1990).

Rand et al. (1985) *J. Arthro. Surg.* 1:242–246 Effect of Electrocautery on Fresh Human Articular Cartilage.

Pearce, John A. (1986) *Electrosurgery*, pp. 17, 69–75, 87, John Wiley & Sons, New York.

Tucker et al. (1989) Abstract P14–11, 7th World Congress on Endourolgy and ESWL, Nov. 27–30, Kyoto, Japan.

* cited by examiner

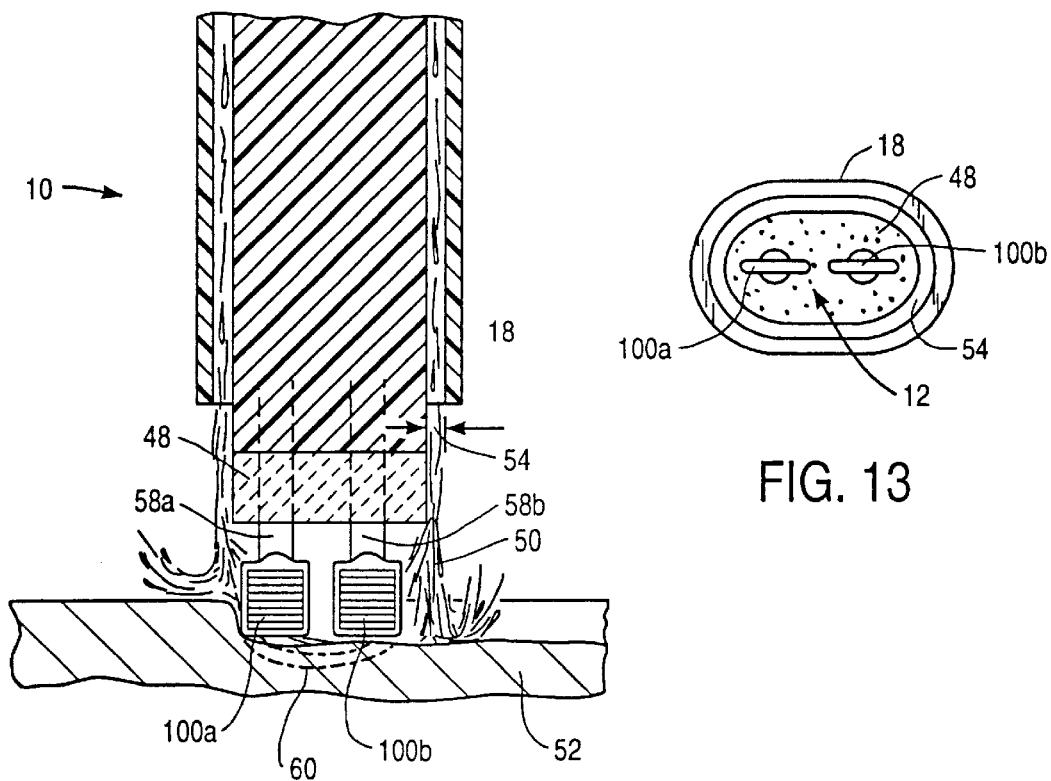
FIG. 13
FIG. 12
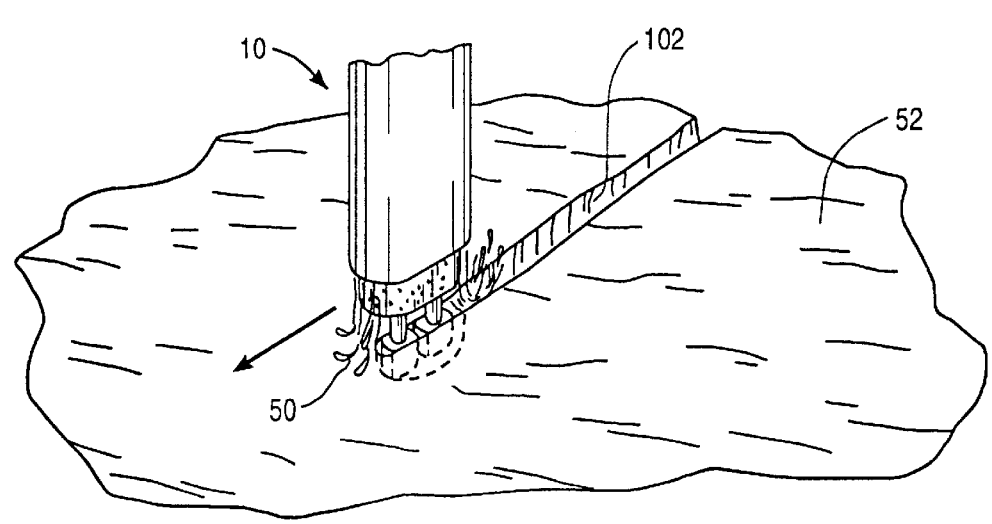
FIG. 14

METHOD FOR TREATING ARTICULAR CARTILAGE DEFECTS

This application is a continuation and claims the benefit of U.S. application Ser. No. 09/177,861, filed Oct. 23, 1998 now U.S. Pat. No. 6,066,134, which is a division of Ser. No. 08/795,686 filed Feb. 5, 1997, now U.S. Pat. No. 5,871,469, which is a division of Ser. No. 08/561,958 filed Nov. 22, 1995, now U.S. Pat. No. 5,697,882, the disclosure of which is incorporated by reference, which is a continuation-in-part of application Ser. No. 08/485,219, filed Jun. 7, 1995 now U.S. Pat. No. 5,697,281, which was a continuation-in-part of PCT International Application, U.S. National Phase Ser. No. PCT/US94/05168, filed on May 10, 1994, which was a continuation-in-part of application Ser. No. 08/059,681, filed on May 10, 1993 U.S. patent # now abandoned, which was a continuation-in-part of application Ser. No. 07/958,977, filed on Oct. 9, 1992 now U.S. Pat. No. 5,366,443, which was a continuation-in-part of application Ser. No. 07/817,575, filed on Jan. 7, 1992 now abandoned, the full disclosures of which are incorporated herein by reference.

BACKGROUND OF THE INVENTION

1. Field of the Invention

The present invention relates generally to the field of electrosurgery and, more particularly, to surgical devices and methods which employ high frequency voltage to cut and ablate tissue.

The field of electrosurgery includes a number of loosely related surgical techniques which have in common the application of electrical energy to modify the structure or integrity of patient tissue. Electrosurgical procedures usually operate through the application of very high frequency currents to cut or ablate tissue structures, where the operation can be monopolar or bipolar. Monopolar techniques rely on external grounding of the patient, where the surgical device defines only a single electrode pole. Bipolar devices comprise both electrodes for the application of current between their surfaces.

Electrosurgical procedures and techniques are particularly advantageous since they generally reduce patient bleeding and trauma associated with cutting operations. Current electrosurgical device and procedures, however, suffer from a number of disadvantages. For example, monopolar devices generally direct electric current along a defined path from the exposed or active electrode through the patient's body to the return electrode, which is externally attached to a suitable location on the patient. This creates the potential danger that the electric current will flow through undefined paths in the patient's body, thereby increasing the risk of unwanted electrical stimulation to portions of the patient's body. In addition, since the defined path through the patient's body has a relatively high impedance (because of the large distance or resistivity of the patient's body), large voltage differences must typically be applied between the return and active electrodes in order to generate a current suitable for ablation or cutting of the target tissue. This current, however, may inadvertently flow along body paths having less impedance than the defined electrical path, which will substantially increase the current flowing through these paths, possibly causing damage to or destroying tissue along and surrounding this pathway.

Bipolar electrosurgical devices have an inherent advantage over monopolar devices because the return current path does not flow through the patient. In bipolar electrosurgical devices, both the active and return electrode are typically exposed so that they may both contact tissue, thereby providing a return current path from the active to the return electrode through the tissue. One drawback with this configuration, however, is that the return electrode may cause tissue desiccation or destruction at its contact point with the patient's tissue. In addition, the active and return electrodes are typically positioned close together to ensure that the return current flows directly from the active to the return electrode. The close proximity of these electrodes generates the danger that the current will short across the electrodes, possibly impairing the electrical control system and/or damaging or destroying surrounding tissue.

The use of electrosurgical procedures (both monopolar and bipolar) in electrically conductive environments can be further problematic. For example, many arthroscopic procedures require flushing of the region to be treated with isotonic saline (also referred to as normal saline), both to maintain an isotonic environment and to keep the field of viewing clear. The presence of saline, which is a highly conductive electrolyte, can also cause shorting of the electrosurgical electrode in both monopolar and bipolar modes. Such shorting causes unnecessary heating in the treatment environment and can further cause non-specific tissue destruction.

Many surgical procedures, such as oral, laparoscopic and open surgical procedures, are not performed with the target tissue submerged under an irrigant. In laparoscopic procedures, such as the resection of the gall bladder from the liver, for example, the abdominal cavity is pressurized with carbon dioxide (pneumoperitoneum) to provide working space for the instruments and to improve the surgeon's visibility of the surgical site. Other procedures, such as the ablation of muscle or gingiva tissue in the mouth, the ablation and necrosis of diseased tissue, or the ablation of epidermal tissue, are also typically performed in a "dry" environment or field (i.e., not submerged under an electrically conducting irrigant).

Present electrosurgical techniques used for tissue ablation also suffer from an inability to control the depth of necrosis in the tissue being treated. Most electrosurgical devices rely on creation of an electric arc between the treating electrode and the tissue being cut or ablated to cause the desired localized heating. Such arcs, however, often create very high temperatures causing a depth of necrosis greater than 500 $\mu$m, frequently greater than 800 $\mu$m, and sometimes as great as 1700 $\mu$m. The inability to control such depth of necrosis is a significant disadvantage in using electrosurgical techniques for tissue ablation, particularly in arthroscopic procedures for ablating and/or reshaping fibrocartilage, articular cartilage, meniscal tissue, and the like.

In an effort to overcome at least some of these limitations of electrosurgery, laser apparatus have been developed for use in arthroscopic and other procedures. Lasers do not suffer from electrical shorting in conductive environments, and certain types of lasers allow for very controlled cutting with limited depth of necrosis. Despite these advantages, laser devices suffer from their own set of deficiencies. In the first place, laser equipment can be very expensive because of the costs associated with the laser light sources. Moreover, those lasers which permit acceptable depths of necrosis (such as eximer lasers, erbium:YAG lasers, and the like) provide a very low volumetric ablation rate, which is a particular disadvantage in cutting and ablation of fibrocartilage, articular cartilage, and meniscal tissue. The holmium:YAG and Nd:YAG lasers provide much higher volumetric ablation rates, but are much less able to control depth of necrosis than are the slower laser devices. The $CO_2$ lasers provide high rate of ablation and low depth of tissue necrosis, but cannot operate in a liquid-filled cavity.

For these and other reasons, improved systems and methods are desired for the electrosurgical ablation and cutting of tissue. These systems and methods should be capable of selectively cutting and ablating tissue and other body structures in electrically conductive environments, such as regions filled with blood or irrigated with electrically conductive solutions, such as isotonic saline, and in relatively dry environments, such as those encountered in oral, dermatological, laparoscopic, thoracosopic and open surgical procedures. Such apparatus and methods should be able to perform cutting and ablation of tissues, while limiting the depth of necrosis and limiting the damage to tissue adjacent to the treatment site.

2. Description of the Background Art

Devices incorporating radio frequency electrodes for use in electrosurgical and electrocautery techniques are described in Rand et al. (1985) J. Arthro. Surg. 1:242–246 and U.S. Pat. Nos. 5,281,216; 4,943,290; 4,936,301; 4,593, 691; 4,228,800; and 4,202,337. U.S. Pat. Nos. 4,943,290 and 4,036,301 describe methods for injecting non-conducting liquid over the tip of a monopolar electrosurgical electrode to electrically isolate the electrode, while energized, from a surrounding electrically conducting irrigant. U.S. Pat. Nos. 5,195,959 and 4,674,499 describe monopolar and bipolar electrosurgical devices, respectively, that include a conduit for irrigating the surgical site.

U.S. Pat. Nos. 5,217,455, 5,423,803, 5,102,410, 5,282, 797, 5,290,273, 5,304,170, 5,312,395, 5,336,217 describe laser treatment methods for removing abnormal skin cells, such as pigmentations, lesions, soft tissue and the like. U.S. Pat. Nos. 5,445,634 and 5,370,642 describe methods for using laser energy to divide, incise or resect tissue during cosmetic surgery. U.S. Pat. No. 5,261,410 is directed to a method and apparatus for detecting and removing malignant tumor tissue. U.S. Pat. Nos. 5,380,316, 4,658,817, 5,389, 096, PCT application No. WO 94/14383 and European Patent Application No. 0 515 867 describe methods and apparatus for percutaneous myocardial revascularization. These methods and apparatus involve directing laser energy against the heart tissue to form transverse channels through the myocardium to increase blood flow from the ventricular cavity to the myocardium.

SUMMARY OF THE INVENTION

The present invention provides a system and method for selectively applying electrical energy to structures within or on the surface of a patient's body. The system and method allow the surgical team to perform electrosurgical interventions, such as ablation and cutting of body structures, while limiting the depth of necrosis and limiting damage to tissue adjacent the treatment site. The system and method of the present invention are useful for surgical procedures in relatively dry environments, such as treating and shaping gingiva, for tissue dissection, e.g. separation of gall bladder from the liver, ablation and necrosis of diseased tissue, such as fibroid tumors, and dermatological procedures involving surface tissue ablation on the epidermis, such as scar or tattoo removal, tissue rejuvenation and the like. The present invention may also be useful in electrically conducting environments, such as arthroscopic or cystoscopic surgical procedures. In addition, the present invention is useful for canalizing or boring channels or holes through tissue, such as the ventricular wall of the heart during transmyocardial revascularization procedures.

The method of the present invention comprises positioning an electrosurgical probe adjacent the target tissue so that at least one active electrode is brought into close proximity to the target site. A return electrode is positioned within an electrically conducting liquid, such as isotonic saline, to generate a current flow path between the target site and the return electrode. High frequency voltage is then applied between the active and return electrode through the current flow path created by the electrically conducting liquid in either a bipolar or monopolar manner. The probe may then be translated, reciprocated or otherwise manipulated to cut the tissue or effect the desired depth of ablation.

The current flow path may be generated by submerging the tissue site in an electrical conducting fluid (e.g., arthroscopic surgery and the like) or by directing an electrically conducting liquid along a fluid path past the return electrode and to the target site to generate the current flow path between the target site and the return electrode. This latter method is particularly effective in a dry environment (i.e., the tissue is not submerged in fluid), such as open, endoscopic or oral surgery, because the electrically conducting liquid provides a suitable current flow path from the target site to the return electrode. The active electrode is preferably disposed at the distal end of the probe and the return electrode is spaced from the active electrode and enclosed within an insulating sheath. This minimizes exposure of the return electrode to surrounding tissue and minimizes possible shorting of the current between the active and return electrodes. In oral procedures, the probe may be introduced directly into the cavity of the open mouth so that the active electrode is positioned against gingival or mucosal tissue. In endoscopic procedures, the probe will typically be passed through a conventional trocar cannula while viewing of the operative site is provided through the use of a laparoscope disposed in a separate cannula.

In a specific aspect of the invention, the high frequency voltage applied between the active and return electrodes generates high voltage gradients in the vicinity of the probe tip. These high voltage gradients are sufficient to create an electric field at the distal boundary of the active electrode(s) that is sufficiently high to break down the tissue through molecular dissociation or disintegration. The high frequency voltage imparts energy to the target site to ablate a thin layer of tissue without causing substantial tissue necrosis beyond the boundary of the thin layer of tissue ablated. This ablative process can be precisely controlled to effect the volumetric removal of tissue as thin as a few layers of cells with minimal heating of or damage to surrounding or underlying tissue structures.

Applicants believe that this precisely controlled ablation is at least partly caused by the high electric field generated around the tip of the active electrode(s) within the electrically conductive liquid. The electric field vaporizes the electrically conductive liquid into a thin layer over at least a portion of the active electrode surface and then ionizes the vapor layer due to the presence of an ionizable species within the liquid. This ionization and the presence of high electric fields in a low density vaporized layer induces the discharge of highly energetic electrons and photons in the form of ultraviolet energy from the vapor layer. The ultraviolet energy and/or energetic electrons cause disintegration of the tissue molecules adjacent to the vapor layer. This energy discharge can be precisely controlled to effect the volumetric removal of tissue thicknesses ranging from millimeters to a few layers of cells without heating or otherwise damaging surrounding or underlying cell structures.

The active electrode(s) will be spaced away from the target tissue by a suitable distance during the ablation process. This spacing allows for the continual resupply of electrically conducting liquid at the interface between the active electrode(s) and the target tissue surface. This continual resupply of the electrically conducting liquid helps to ensure that the thin vapor layer or region will remain over at least a portion of the active electrode(s) between the active electrode(s) and the tissue surface. Preferably, the active electrode(s) will be translated and/or rotated transversely relative to the tissue, i.e., in a light brushing motion, to maintain the supply of electrically conducting fluid in the region between the active electrode(s) and the tissue. This dynamic movement of the active electrode(s) over the tissue site also allows the electrically conducting liquid to cool the tissue surrounding recently ablated areas to minimize damage to this surrounding tissue.

The apparatus according to the present invention comprises an electrosurgical probe having a shaft with a proximal end, a distal end, and at least one active electrode at or near the distal end. A connector is provided at or near the proximal end of the shaft for electrically coupling the active electrode to a high frequency voltage source. A return electrode coupled to the voltage source is spaced a sufficient distance from the active electrode to substantially avoid or minimize current shorting therebetween and, in dry environments, to shield the return electrode from tissue at the target site of ablation or from the surgeon. In irrigant flooded environments, such as arthroscopic surgery, the area of the return electrode is sufficiently large to result in low current densities that effectively preclude damage to nearby tissue. The return electrode may be provided integral with the shaft of the probe or it may be separate from the shaft (e.g., on a liquid supply instrument). In both cases, the return electrode defines an inner, annular surface of the pathway for flow of electrically conducting liquid therethrough. The liquid is directed past the surface of the return electrode and over the active electrode to thereby provide a return current flow path between the target tissue site and the return electrode.

The active and return electrodes will preferably be configured such that, upon the application of a sufficient high-frequency voltage, a thin layer of the electrically conducting layer is vaporized over at least a portion of the active electrode(s) in the region between the active electrode(s) and the target tissue. To accomplish this, the active electrode(s) will be configured such that high electric field densities form at the distal tips of the active electrode(s). By way of example, the present invention may utilize an electrode array of electrode terminals flush with or recessed from or extending from the distal end of the probe. The electrode terminals will preferably have a sufficiently small area, extension (or recession) length from the probe and sharp edges and/or surface asperities such that localized high current densities are promoted on the electrode terminals which, in turn, lead to the formation of a vaporized layer or region over at least a portion of the active electrode(s) followed by the high electric field induced breakdown (i.e., ionization) of ionizable species within the vapor layer or region and the emission of photon and/or electrons of sufficient energy to cause dissociation of molecules within the target tissue.

In an exemplary embodiment, the active electrode(s) are sized and arranged to create localized sources of energy (e.g., point sources or sources with a relatively small effective radius) at the distal tips of the electrode(s) when a sufficiently high frequency voltage is applied to the return and active electrodes. These small localized sources generate intense energy at the distal ends of the electrodes for molecular dissociation or ablation of tissue in contact with or in close proximity to the electrode tips. In addition, since the localized sources have relatively small radii, the energy flux decreases with the square of the distance from the localized sources so that the tissue at greater distances from the electrode tips are not significantly affected by the energy flux.

A further understanding of the nature and advantages of the invention will become apparent by reference to the remaining portions of the specification and drawings.

BRIEF DESCRIPTION OF THE DRAWINGS

FIG. 12 is a schematic view of an electrosurgical probe having two screwdriver-shaped electrodes extending from the distal end;

FIG. 13 is an end view of the probe of FIG. 12;

FIG. 14 illustrates use of the probe of FIG. 12 for the rapid cutting of tissue;

DESCRIPTION OF THE PREFERRED EMBODIMENT

Figure 1:
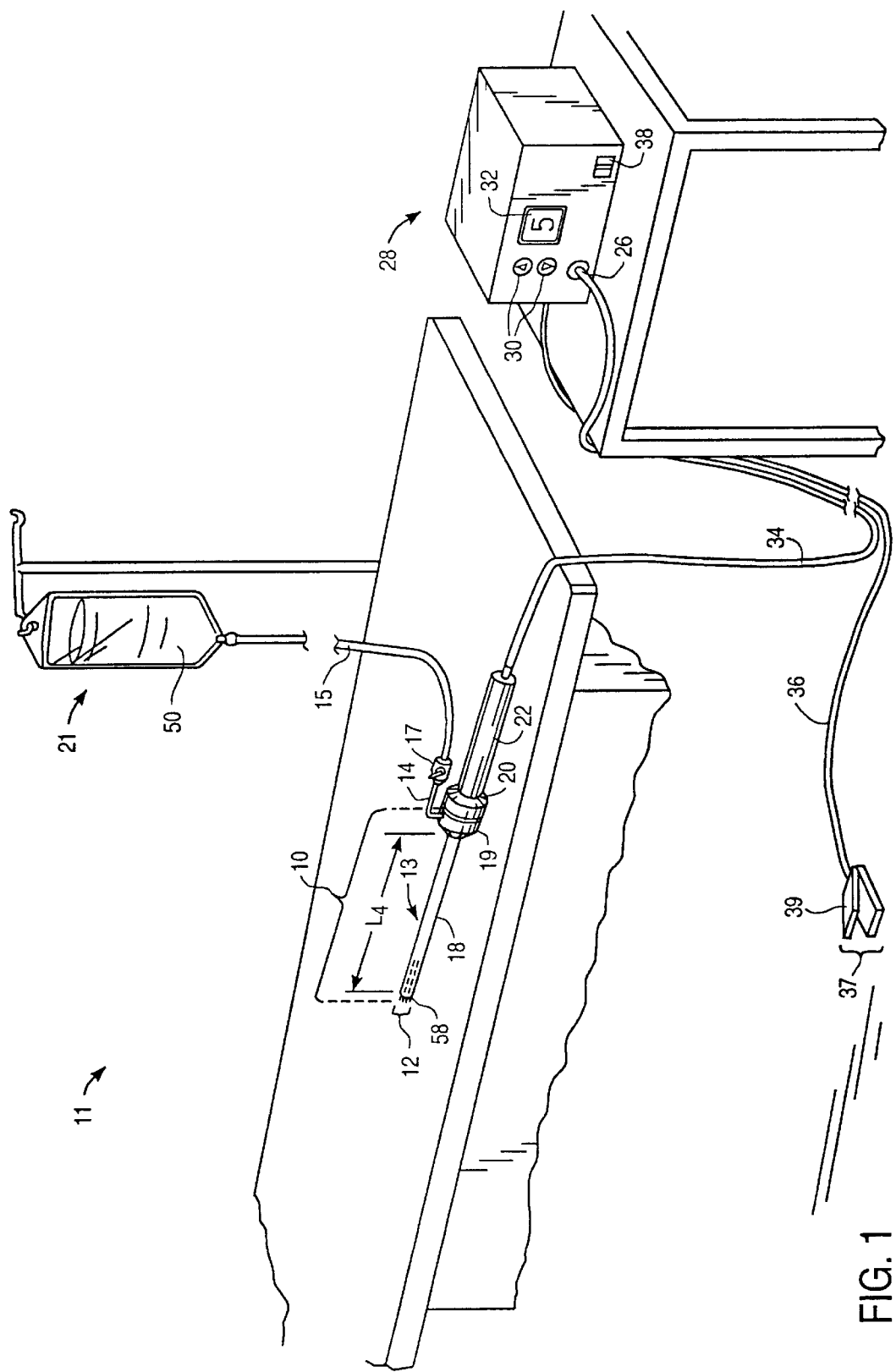
FIG. 1 is a perspective view of the electrosurgical system including an electrosurgical probe, an electrically conducting liquid supply and an electrosurgical power supply constructed in accordance with the principles of the present invention.

The present invention provides a system and method for selectively applying electrical energy to a target location within or on a patient's body, such as solid tissue or the like, particularly including gingival tissues and mucosal tissues located in the mouth or epidermal tissue on the outer skin. In addition, tissues which may be treated by the system and method of the present invention include tumors, abnormal tissues, and the like. The invention may also be used for canalizing or boring channels or holes through tissue, such as the ventricular wall during transmyocardial revascularization procedures. For convenience, the remaining disclosure will be directed specifically to the cutting, shaping or ablation of gingival or mucosal tissue in oral surgical procedures, the surface tissue ablation of the epidermis in dermatological procedures and the canalization of channels through the myocardium of the heart, but it will be appreciated that the system and method can be applied equally well to procedures involving other tissues of the body, as well as to other procedures including open surgery, laparoscopic surgery, thoracoscopic surgery, and other endoscopic surgical procedures.

The present invention is also useful for cutting, shaping or ablation of fibrocartilage and articular cartilage during arthroscopic or endoscopic procedure. The target tissue will be, by way of example but not limited to, articular cartilage, fibrocartilage, and meniscal tissue, such as found in the joints of the knee, shoulder, hip, foot, hand and spine.

In addition, the present invention is particularly useful in procedures where the tissue site is flooded or submerged with an electrically conducting fluid, such as isotonic saline. Such procedures, e.g., arthroscopic surgery and the like, are described in detail in co-pending PCT International Application, U.S. National Phase Serial No. PCT/US94/05168, filed on May 10, 1994, the complete disclosure of which has been incorporated herein by reference.

The present invention may use a single active electrode or an electrode array distributed over a distal contact surface of a probe. The electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive liquids, such as blood, normal saline, and the like. The electrode terminals may be independently current-limited by using isolating the terminals from each other and connecting each terminal to a separate power source that is isolated from the other electrode terminals. Alternatively, the electrode terminals may be connected to each other at either the proximal or distal ends of the probe to form a single wire that couples to a power source.

The electrosurgical probe will comprise a shaft having a proximal end and a distal end which supports an active electrode. The shaft may assume a wide variety of configurations, with the primary purpose being to mechanically support the active electrode and permit the treating physician to manipulate the electrode from a proximal end of the shaft. Usually, the shaft will be a narrow-diameter rod or tube, more usually having dimensions which permit it to be introduced into a body cavity, such as the mouth or the abdominal cavity, through an associated trocar or cannula in a minimally invasive procedure, such as arthroscopic, laparoscopic, thoracoscopic, and other endoscopic procedures. Thus, the shaft will typically have a length of at least 5 cm for oral procedures and at least 10 cm, more typically being 20 cm, or longer for endoscopic procedures. The shaft will typically have a diameter of at least 1 mm and frequently in the range from 1 to 10 mm. Of course, for dermatological procedures on the outer skin, the shaft may have any suitable length and diameter that would facilitate handling by the surgeon.

The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft. Specific shaft designs will be described in detail in connection with the figures hereinafter.

The circumscribed area of the electrode array is in the range from 0.25 mm$^2$ to 75 mm$^2$, preferably from 0.5 mm$^2$ to 40 mm$^2$, and will usually include at least two isolated electrode terminals, more usually at least four electrode terminals, preferably at least six electrode terminals, and often 50 or more electrode terminals, disposed over the distal contact surfaces on the shaft. By bringing the electrode array(s) on the contact surface(s) in close proximity with the target tissue and applying high frequency voltage between the array(s) and an additional common or return electrode in direct or indirect contact with the patient's body, the target tissue is selectively ablated or cut, permitting selective removal of portions of the target tissue while desirably minimizing the depth of necrosis to surrounding tissue. In particular, this invention provides a method and apparatus for effectively ablating and cutting tissue which may be located in close proximity to other critical organs, vessels or structures (e.g., teeth, bone) by simultaneously (1) causing electrically conducting liquid to flow between the common and active electrodes, (2) applying electrical energy to the target tissue surrounding and immediately adjacent to the tip of the probe, (3) bringing the active electrode(s) in close proximity with the target tissue using the probe itself, and (4) optionally moving the electrode array axially and/or transversely over the tissue.

In one configuration, each individual electrode terminal in the electrode array is electrically insulated from all other electrode terminals in the array within said probe and is connected to a power source which is isolated from each of the other electrodes in the array or to circuitry which limits or interrupts current flow to the electrode when low resistivity material (e.g., blood or electrically conductive saline irrigant) causes a lower impedance path between the common electrode and the individual electrode terminal. The isolated power sources for each individual electrode may be separate power supply circuits having internal impedance characteristics which limit power to the associated electrode terminal when a low impedance return path is encountered, may be a single power source which is connected to each of the electrodes through independently actuatable switches or may be provided by independent current limiting elements, such as inductors, capacitors, resistors and/or combinations thereof. The current limiting elements may be provided in the probe, connectors, cable, controller or along the conductive path from the controller to the distal tip. Alternatively, the resistance and/or capacitance may occur on the surface of the active electrode(s) due to oxide layers which form selected electrode terminals (e.g., titanium or a resistive coating on the surface of metal, such as platinum)

The tip region of the probe may be composed of many independent electrode terminals designed to deliver electrical energy in the vicinity of the tip. The selective application of electrical energy to the target tissue is achieved by connecting each individual electrode terminal and the common electrode to a power source having independently controlled or current limited channels. The common electrode may be a tubular member of conductive material proximal to the electrode array at the tip which also serves as a conduit for the supply of the electrically conducting liquid between the active and common electrodes. The application of high frequency voltage between the common electrode and the electrode array results in the generation of high electric field intensities at the distal tips of the electrodes with conduction of high frequency current from each individual electrode terminal to the common electrode. The current flow from each individual electrode terminal to the common electrode is controlled by either active or passive means, or a combination thereof, to deliver electrical energy to the target tissue while minimizing energy delivery to surrounding (non-target) tissue and any conductive fluids which may be present (e.g., blood, electrolytic irrigants such as saline, and the like).

In a preferred aspect, this invention takes advantage of the differences in electrical resistivity between the target tissue (e.g., gingiva, muscle, fascia, tumor, epidermal, heart or other tissue) and the surrounding conductive liquid (e.g., isotonic saline irrigant). By way of example, for any selected level of applied voltage, if the electrical conduction path between the common electrode and one of the individual electrode terminals within the electrode array is isotonic saline irrigant liquid (having a relatively low electrical impedance), the current control means connected to the individual electrode will limit current flow so that the heating of intervening conductive liquid is minimized. On the other hand, if a portion of or all of the electrical conduction path between the common electrode and one of the individual electrode terminals within the electrode array is gingival tissue (having a relatively higher electrical impedance), the current control circuitry or switch connected to the individual electrode will allow current flow sufficient for the deposition of electrical energy and associated ablation or electrical breakdown of the target tissue in the immediate vicinity of the electrode surface.

The application of a high frequency voltage between the common or return electrode and the electrode array for appropriate time intervals effects ablation, cutting or reshaping of the target tissue. The tissue volume over which energy is dissipated (i.e., a high voltage gradient exists) may be precisely controlled, for example, by the use of a multiplicity of small electrodes whose effective diameters range from about 2 mm to 0.01 mm, preferably from about 1 mm to 0.05 mm, and more preferably from about 0.5 mm to 0.1 mm. Electrode areas for both circular and non-circular terminals will have a contact area (per electrode) below 5 mm$^2$, preferably being in the range from 0.0001 mm$^2$ to 1 mm$^2$, and more preferably from 0.005 mm$^2$ to 0.5 mm$^2$. The use of small diameter electrode terminals increases the electric field intensity and reduces the extent or depth of tissue necrosis as a consequence of the divergence of current flux lines which emanate from the exposed surface of each electrode terminal. Energy deposition in tissue sufficient for irreversible damage (i.e., necrosis) has been found to be limited to a distance of about one-half to one electrode diameter. This is a particular advantage over prior electrosurgical probes employing single and/or larger electrodes where the depth of tissue necrosis may not be sufficiently limited.

In previous electrosurgical devices, increased power application and ablation rates have been achieved by increasing the electrode area. Surprisingly, with the present invention, it has been found that the total electrode area can be increased (to increase power delivery and ablation rate) without increasing the depth of necrosis by providing multiple small electrode terminals. Preferably, the terminals will be spaced-apart by a distance in the range from about one-half diameter to one diameter for optimum power delivery, as discussed below. The depth of necrosis may be further controlled by switching the applied voltage off and on to produce pulses of current, the pulses being of sufficient duration and associated energy density to effect ablation and/or cutting while being turned off for periods sufficiently long to allow for thermal relaxation between energy pulses. In this manner, the energy pulse duration and magnitude and the time interval between energy pulses are selected to achieve efficient rates of tissue ablation or cutting while allowing the temperature of the treated zone of tissue to "relax" or return to normal physiologic temperatures (usually to within 10° C. of normal body temperature [37° C.], preferably to within 5° C.) before the onset of the next energy (current) pulse.

In addition to the above described methods, the applicant has discovered another mechanism for ablating tissue while minimizing the depth of necrosis. This mechanism involves applying a high frequency voltage between the active electrode surface and the return electrode to develop high electric field intensities in the vicinity of the target tissue site. The high electric field intensities lead to electric field induced molecular breakdown of target tissue through molecular dissociation (rather than thermal evaporation or carbonization). In other words, the tissue structure is volumetrically removed through molecular disintegration of complex organic molecules into non-viable hydrocarbons and nitrogen compounds. This molecular disintegration completely removes the tissue structure, as opposed to transforming the tissue material from a solid form directly to a vapor form, as is typically the case with ablation.

The high electric field intensities may be generated by applying a high frequency voltage that is sufficient to vaporize the electrically conducting liquid over at least a portion of the active electrode(s) in the region between the distal tip of the active electrode and the target tissue. Since the vapor layer or vaporized region has a relatively high electrical impedance, it increases the voltages differential between the active electrode tip and the tissue and causes ionization within the vapor layer due to the presence of an ionizable species (e.g., sodium when isotonic saline is the electrically conducting fluid). This ionization, under optimal conditions, induces the discharge of energetic electrons and photons from vapor layer and to the surface of the target tissue. This energy may be in the form of energetic photons (e.g., ultraviolet radiation), energetic particles (e.g., electrons) or a combination thereof.

The necessary conditions for forming a vapor layer near the active electrode tip(s), ionizing the atom or atoms within the vapor layer and inducing the discharge of energy from plasma within the vapor layer will depend on a variety of factors, such as: the number of electrode terminals; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Based on initial experiments, applicants believe that the ionization of atoms within the vapor layer produced in isotonic saline (containing sodium chloride) leads to the generation of energetic photons having wavelengths, by way of example, in the range of 306 to 315 nanometers (ultraviolet spectrum) and 588 to 590 nanometers (visible spectrum). In addition, the free electrons within the ionized vapor layer are accelerated in the high electric fields near the electrode tip(s). When the density of the vapor layer (or within a bubble formed in the electrically conducting liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Energy evolved by the energetic electrons (e.g., 4 to 5 eV) can subsequently bombard a molecule and break its bonds, dissociating a molecule into free radicals, which then combine into final gaseous or liquid species.

The photon energy produces photoablation through photochemical and/or photothermal processes to disintegrate tissue thicknesses as small as several cell layers of tissue at the target site. This photoablation is a "cold" ablation, which means that the photon energy transfers very little heat to tissue beyond the boundaries of the region of tissue ablated. The cold ablation provided by photon energy can be precisely controlled to only affect a thin layer of cells without heating or otherwise damaging surrounding or underlying cells. The depth of necrosis will be typically be about 0 to 400 microns and usually 10 to 200 microns. Applicants believe that the "fragments" of disintegrated tissue molecules carry away much of the energy which is deposited on the surface of the target tissue, thereby allowing molecular disintegration of tissue to occur while limiting the amount of heat transfer to the surrounding tissue.

In addition, other competing mechanisms may be contributing to the ablation of tissue. For example, tissue destruction or ablation may also be caused by dielectric breakdown of the tissue structural elements or cell membranes from the highly concentrated intense electric fields at the tip portions of the electrode(s). According to the teachings of the present invention, the active electrode(s) are sized and have exposed surfaces areas which, under proper conditions of applied voltage, cause the formation of a vaporized region or layer over at least a portion of the surface of the active electrode(s). This layer or region of vaporized electrically conducting liquid creates the conditions necessary for ionization within the vaporized region or layer and the generation of energetic electrons and photons. In addition, this layer or region of vaporized electrically conducting liquid provides a high electrical impedance between the electrode and the adjacent tissue so that only low levels of current flow across the vaporized layer or region into the tissue, thereby minimizing joulean heating in, and associated necrosis of, the tissue.

As discussed above, applicants have found that the density of the electrically conducting liquid at the distal tips of the active electrodes should be less than a critical value to form a suitable vapor layer. For aqueous solutions, such as water or isotonic saline, this upper density limit is approximately $10^{20}$ atoms/cm$^3$, which corresponds to about $3\times10^{-3}$ grams/cm$^3$. Applicant's also believe that once the density in the vapor layer reaches a critical value (e.g., approximately $10^{20}$ atoms/cm$^3$ for aqueous solutions), electron avalanche occurs. The growth of this avalanche is retarded when the space charge generated fields are on the order of the external field. Spatial extent of this region should be larger than the distance required for an electron avalanche to become critical and for an ionization front to develop. This ionization front develops and propagates across the vapor layer via a sequence of processes occurring the region ahead of the front, viz, heat by electron injection, lowering of the local liquid density below the critical value and avalanche growth of the charged particle concentration.

Electrons accelerated in the electric field within the vapor layer will apparently become trapped after one or a few scatterings. These injected electrons serve to create or sustain a low density region with a large mean free path to enable subsequently injected electrons to cause impact ionization within these regions of low density. The energy evolved at each recombination is on the order of half of the energy band gap (i.e., 4 to 5 eV). It appears that this energy can be transferred to another electron to generate a highly energetic electron. This second, highly energetic electron may have sufficient energy to bombard a molecule to break its bonds, i.e., dissociate the molecule into free radicals.

The electrically conducting liquid should have a threshold conductivity in order to suitably ionize the vapor layer for the inducement of energetic electrons and photons. The electrical conductivity of the fluid (in units of milliSiemans per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm. The electrical conductivity of the channel trailing the ionization front should be sufficiently high to maintain the energy flow required to heat the liquid at the ionization front and maintain its density below the critical level. In addition, when the electrical conductivity of the liquid is sufficiently high, ionic pre-breakdown current levels (i.e., current levels prior to the initiation of ionization within the vapor layer) are sufficient to also promote the initial growth of bubbles within the electrically conducting liquid (i.e., regions whose density is less than the critical density).

Asperities on the surface of the active electrode(s) appear to promote localized high current densities which, in turn, promote bubble nucleation at the site of the asperities whose enclosed density (i.e., vapor density) is below the critical density to initiate ionization breakdown within the bubble. Hence, a specific configuration of the present invention creates regions of high current densities on the tips of the electrode(s) (i.e., the surface of the electrode(s) which are to engage and ablate or cut tissue). Regions of high current densities can be achieved via a variety of methods, such as producing sharp edges and corners on the distal tips of the electrodes or vapor blasting, chemically etching or mechanically abrading the distal end faces of the active electrodes to produce surface asperities thereon. Alternatively, the electrode terminals may be specifically designed to increase the edge/surface area ratio of the electrode terminals. For example, the electrode terminal(s) may be hollow tubes having a distal, circumferential edge surrounding an opening. The terminals may be formed in an array as described above or in a series of concentric terminals on the distal end of the probe. High current densities will be generated around the circumferential edges of the electrode terminals to promote nucleate bubble formation.

The voltage applied between the common electrode and the electrode array will be at high or radio frequency, typically between about 5 kHz and 20 MHz, usually being between about 30 kHz and 2.5 MHz, and preferably being between about 50 kHz and 400 kHz. The RMS (root mean square) voltage applied will usually be in the range from about 5 volts to 1000 volts, preferably being in the range from about 50 volts to 800 volts, and more preferably being in the range from about 100 volts to 400 volts. These frequencies and voltages will result in peak-to-peak voltages and current that are sufficient to vaporize the electrically conductive liquid and, in turn, create the conditions within the vaporized region which result in high electric fields and emission of energetic photons and/or electrons to ablate tissue. Typically, the peak-to-peak voltage will be in the range of 200 to 2000 volts and preferably in the range of 300 to 1400 volts and more preferably in the range of 700 to 900 volts.

As discussed above, the voltage is usually delivered in a series of voltage pulses with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the pulsed laser duty cycle (i.e., cumulative time in any one-second interval that energy is applied) is on the order of about 50% for the present invention, as compared with lasers which typically have a duty cycle of about 0.0001%.

Applicants believe that the present invention is capable of obtaining high ablation rates with effectively continuous mode operation and high duty cycles because the source of energy emitted from the edges and tips of the small electrode terminals is effectively a point source or a source having a relatively small effective radius. As is well known in the art, the flux emitted from a point source and crossing a boundary in spherical space generally decreases as the square of distance from the source. Thus, the "energy source" of the present invention (i.e., the intense electric field, the energetic photons or the energetic electrons) is highly concentrated by virtue of the geometry of the emitting electrodes and the source of energy at the tips of the electrodes. As a result, only those regions or areas that are very close to the electrode tips or source will be exposed to high energy fluxes. Consequently, ablation will typically only occur in tissue layers effectively in contact or in very close proximity with the tips of the electrodes. The tissue at greater distances from the electrode tips are not significantly affected since the energy flux is too low at these distances to irreversibly affect or damage tissue.

Usually, the current level will be selectively limited or controlled and the voltage applied will be independently adjustable, frequently in response to the resistance of tissues and/or fluids in the pathway between an individual electrode and the common electrode. Also, the applied current level may be in response to a temperature control means which maintains the target tissue temperature with desired limits at the interface between the electrode arrays and the target tissue. The desired tissue temperature along a propagating surface just beyond the region of ablation will usually be in the range from about 40° C. to 100° C., and more usually from about 50° C. to 60° C. The tissue being ablated (and hence removed from the operation site) immediately adjacent the electrode array may reach even higher temperatures.

The preferred power source of the present invention delivers a high frequency current selectable to generate average power levels ranging from tens of milliwatts to tens of watts per electrode, depending on the target tissue being ablated, the rate of ablation desired or the maximum allowed temperature selected for the probe tip. The power source allows the user to select the current level according to the specific requirements of a particular oral surgery, dermatological procedure, open surgery or other endoscopic surgery procedure.

The power source may be current limited or otherwise controlled so that undesired heating of electrically conductive fluids or other low electrical resistance media does not occur. In a presently preferred embodiment of the present invention, current limiting inductors are placed in series with each independent electrode terminal, where the inductance of the inductor is in the range of 10 uH to 50,000 uH, depending on the electrical properties of the target tissue, the desired ablation rate and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual electrode in contact with a low resistance medium (e.g., saline irrigant), the resistance of the current limiting resistor increases significantly, thereby minimizing the power delivery from said electrode into the low resistance medium (e.g., saline irrigant).

As an alternative to such passive circuit structures, regulated current flow to each electrode terminal may be provided by a multi-channel power supply. A substantially constant current level for each individual electrode terminal within a range which will limit power delivery through a low resistance path, e.g., isotonic saline irrigant, and would be selected by the user to achieve the desired rate of cutting or ablation. Such a multi-channel power supply thus provides a substantially constant current source with selectable current level in series with each electrode terminal, wherein all electrodes will operate at or below the same, user selectable maximum current level. Current flow to all electrode terminals could be periodically sensed and stopped if the temperature measured at the surface of the electrode array exceeds user selected limits. Particular control system designs for implementing this strategy are well within the skill of the art.

Yet another alternative involves the use of one or several power supplies which allow one or several electrodes to be simultaneously energized and which include active control means for limiting current levels below a preselected maximum level. In this arrangement, only one or several electrodes would be simultaneously energized for a brief period. Switching means would allow the next one or several electrodes to be energized for a brief period. By sequentially energizing one or several electrodes, the interaction between adjacent electrodes can be minimized (for the case of energizing several electrode positioned at the maximum possible spacing within the overall envelope of the electrode array) or eliminated (for the case of energizing only a single electrode at any one time). As before, a resistance measurement means may be employed for each electrode prior to the application of power wherein a (measured) low resistance (below some preselected level) will prevent that electrode from being energized during a given cycle. By way of example, the sequential powering and control scheme of the present invention would function in a manner similar to an automobile distributor. In this example, an electrical contact rotates past terminals connected to each spark plug. In this example, each spark plug corresponds to the exposed surface of each of the electrodes. In addition, the present invention includes the means to measure the resistance of the medium in contact with each electrode and cause voltage to be applied only if the resistance exceeds a preselected level.

It should be clearly understood that the invention is not limited to electrically isolated electrode terminals, or even to a plurality of electrode terminals. For example, the array of active electrode terminals may be connected to a single lead that extends through the probe shaft to a power source of high frequency current. Alternatively, the probe may incorporate a single electrode that extends directly through the probe shaft or is connected to a single lead that extends to the power source.

The active electrode(s) are formed over a contact surface on the shaft of the electrosurgical probe. The common (return) electrode surface will be recessed relative to the distal end of the probe and may be recessed within the conduit provided for the introduction of electrically conducting liquid to the site of the target tissue and active electrode(s). In the exemplary embodiment, the shaft will be cylindrical over most of its length, with the contact surface being formed at the distal end of the shaft. In the case of endoscopic applications, the contact surface may be recessed since it helps protect and shield the electrode terminals on the surface while they are being introduced, particularly while being introduced through the working channel of a trocar channel or a viewing scope.

The area of the contact surface can vary widely, and the contact surface can assume a variety of geometries, with particular areas in geometries being selected for specific applications. Active electrode contact surfaces can have areas in the range from 0.25 mm$^2$ to 50 mm$^2$, usually being from 1 mm$^2$ to 20 mm$^2$. The geometries can be planar, concave, convex, hemispherical, conical, linear "in-line" array or virtually any other regular or irregular shape. Most commonly, the active electrode(s) will be formed at the distal tip of the electrosurgical probe shaft, frequently being planar, disk-shaped, or hemispherical surfaces for use in reshaping procedures or being linear arrays for use in cutting. Alternatively or additionally, the active electrodes) may be formed on lateral surfaces of the electrosurgical probe shaft (e.g., in the manner of a spatula), facilitating access to certain body structures in electrosurgical procedures.

During the surgical procedure, the distal end of the probe or the active electrode(s) will be maintained at a small distance away from the target tissue surface. This small spacing allows for the continual resupply of electrically conducting liquid into the interface between the active electrode(s) and the target tissue surface. This continual resupply of the electrically conducting liquid helps to ensure that the thin vapor layer will remain between active electrode(s) and the tissue surface. In addition, dynamic movement of the active electrode(s) over the tissue site allows the electrically conducting liquid to cool the tissue surrounding recently ablated areas to minimize thermal damage to this surrounding tissue. Typically, the active electrode(s) will be about 0.02 to 2 mm from the target tissue and preferably about 0.05 to 0.5 mm during the ablation process. One method of maintaining this space is to translate and/or rotate the probe transversely relative to the tissue, i.e., a light brushing motion, to maintain a thin vaporized layer or region between the active electrode and the tissue. Of course, if coagulation of a deeper region of tissue is necessary (e.g., for sealing a bleeding vessel imbedded within the tissue), it may be desirable to press the active electrode against the tissue to effect joulean heating therein.

Referring to the drawings in detail, wherein like numerals indicate like elements, an electrosurgical system 11 is shown constructed according to the principles of the present invention. Electrosurgical system 11 generally comprises an electrosurgical probe 10 connected to a power supply 28 for providing high frequency voltage to a target tissue 52 and a liquid source 21 for supplying electrically conducting fluid 50 to probe 10.

In an exemplary embodiment as shown in FIG. 1, electrosurgical probe 10 includes an elongated shaft 13 which may be flexible or rigid, with flexible shafts optionally including support cannulas or other structures (not shown). Probe 10 includes a connector 19 at its proximal end and an array 12 of electrode terminals 58 disposed on the distal tip of shaft 13. A connecting cable 34 has a handle 22 with a connector 20 which can be removably connected to connector 19 of probe 10. The proximal portion of cable 34 has a connector 26 to couple probe 10 to power supply 28. The electrode terminals 58 are electrically isolated from each other and each of the terminals 58 is connected to an active or passive control network within power supply 28 by means of a plurality of individually insulated conductors 42 (see FIG. 2C). Power supply 28 has a selection means 30 to change the applied voltage level. Power supply 28 also includes means for energizing the electrodes 58 of probe 10 through the depression of a pedal 39 in a foot pedal 37 positioned close to the user. The foot pedal 37 may also include a second pedal (not shown) for remotely adjusting the energy level applied to electrodes 58. The specific design of a power supply which may be used with the electrosurgical probe of the present invention is described in parent application PCT US 94/051,168, the full disclosure of which has previously been incorporated herein by reference.

Figure 2A:
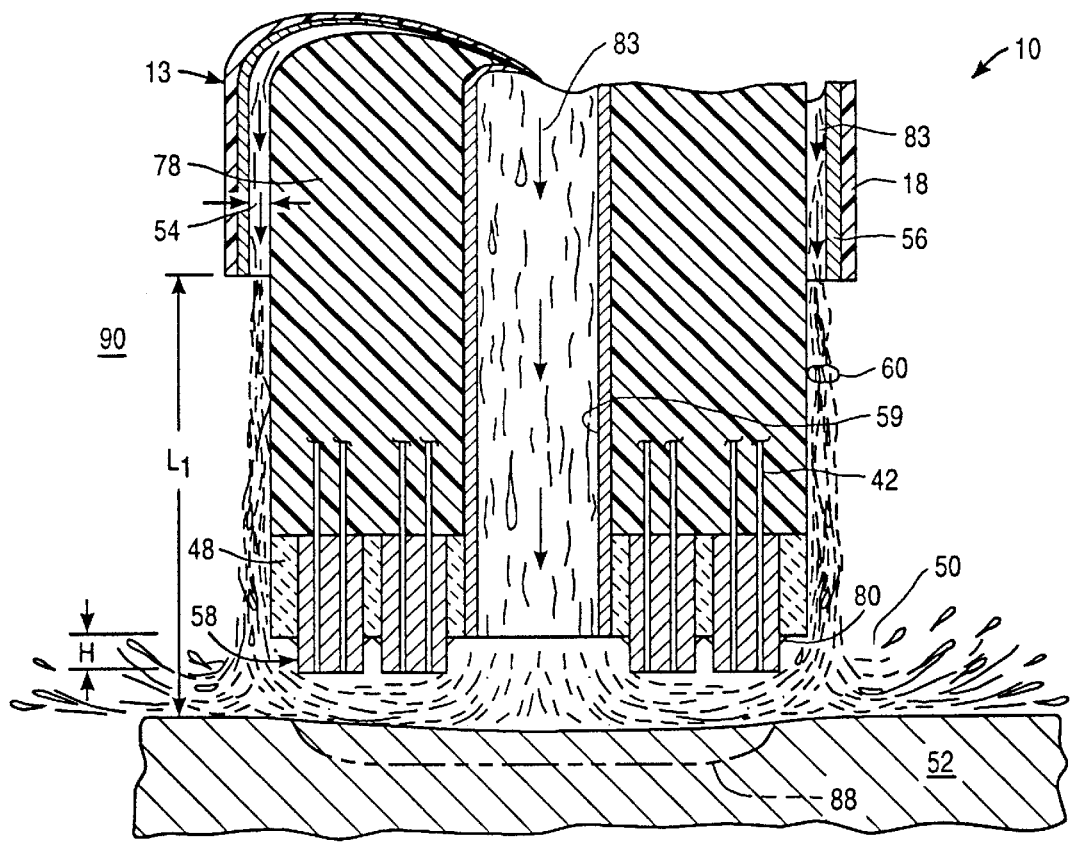
FIG. 2A is an enlarged, cross-sectional view of the distal tip of the electrosurgical probe of FIG. 1 illustrating an electrode arrangement suitable for rapid cutting and ablation of tissue structures.
Figure 2B:
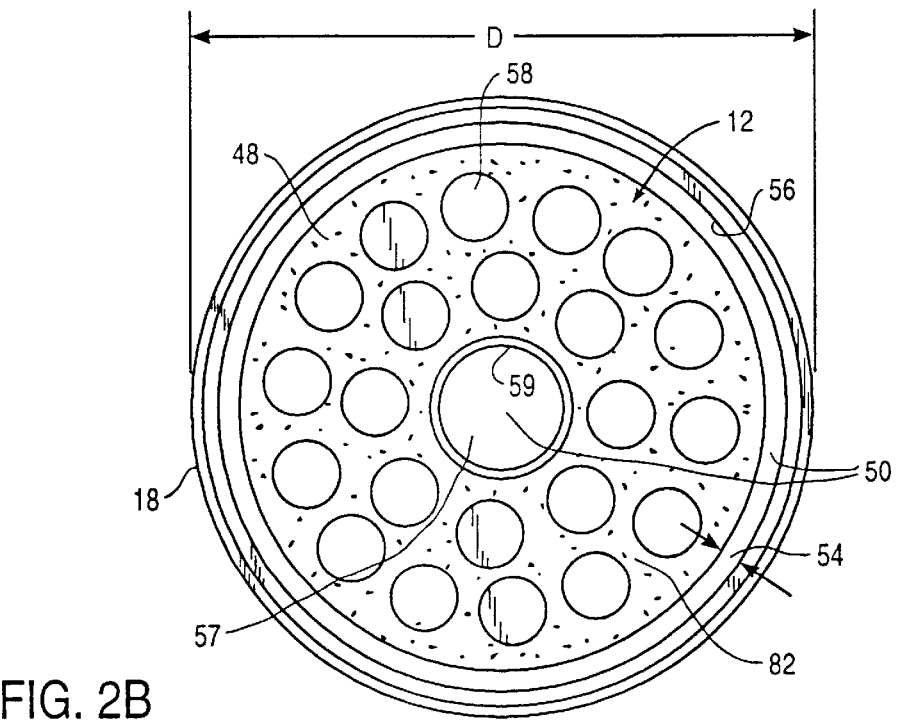
FIG. 2B is an enlarged end view of the distal tip of the electrosurgical probe of FIG. 1.
Figure 5:
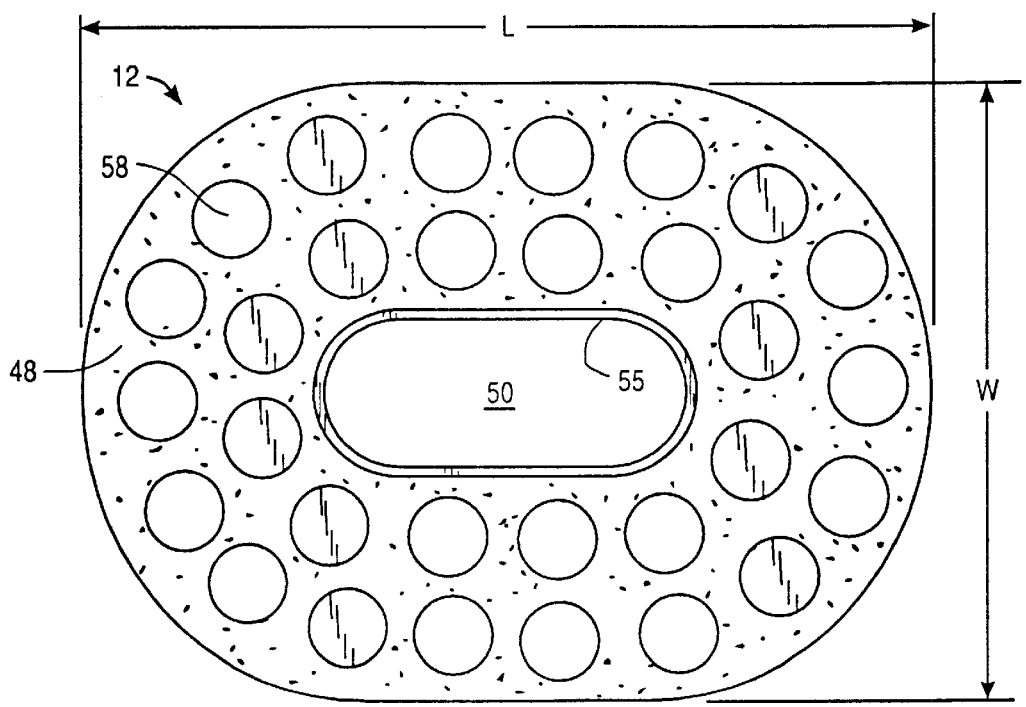
FIG. 5 is an end view of an another embodiment of the electrosurgical probe of FIG. 1.

Referring to FIGS. 2A and 2B, the electrically isolated electrode terminals 58 are spaced-apart over an electrode array surface 82. The electrode array surface 82 and individual electrode terminals 58 will usually have dimensions within the ranges set forth above. In the preferred embodiment, the electrode array surface 82 has a circular cross-sectional shape with a diameter D (FIG. 2B) in the range from 0.3 mm to 10 mm. Electrode array surface 82 may also have an oval shape, having a length L in the range of 1 mm to 20 mm and a width W in the range from 0.3 mm to 7 mm, as shown in FIG. 5. The individual electrode terminals 58 will protrude over the electrode array surface 82 by a distance (H) from 0 mm to 2 mm, preferably from 0 mm to 1 mm (see FIG. 3).

It should be noted that the electrode terminals may be flush with the electrode array surface 82, or the terminals may be recessed from the surface. For example, in dermatological procedures, the electrode terminals 58 may be recessed by a distance from 0.01 mm to 1 mm, preferably 0.01 mm to 0.2 mm. In one embodiment of the invention, the electrode terminals are axially adjustable relative to the electrode array surface 82 so that the surgeon can adjust the distance between the surface and the electrode terminals.

The electrode terminals 58 are preferably composed of a refractory, electrically conductive metal or alloy, such as platinum, titanium, tantalum, tungsten and the like. As shown in FIG. 2B, the electrode terminals 58 are anchored in a support matrix 48 of suitable insulating material (e.g., ceramic or glass material, such as alumina, zirconia and the like) which could be formed at the time of manufacture in a flat, hemispherical or other shape according to the requirements of a particular procedure. The preferred support matrix material is alumina, available from Kyocera Industrial Ceramics Corporation, Elkgrove, Ill., because of its high thermal conductivity, good electrically insulative properties, high flexural modulus, resistance to carbon tracking, biocompatibility, and high melting point.

Figure 3:
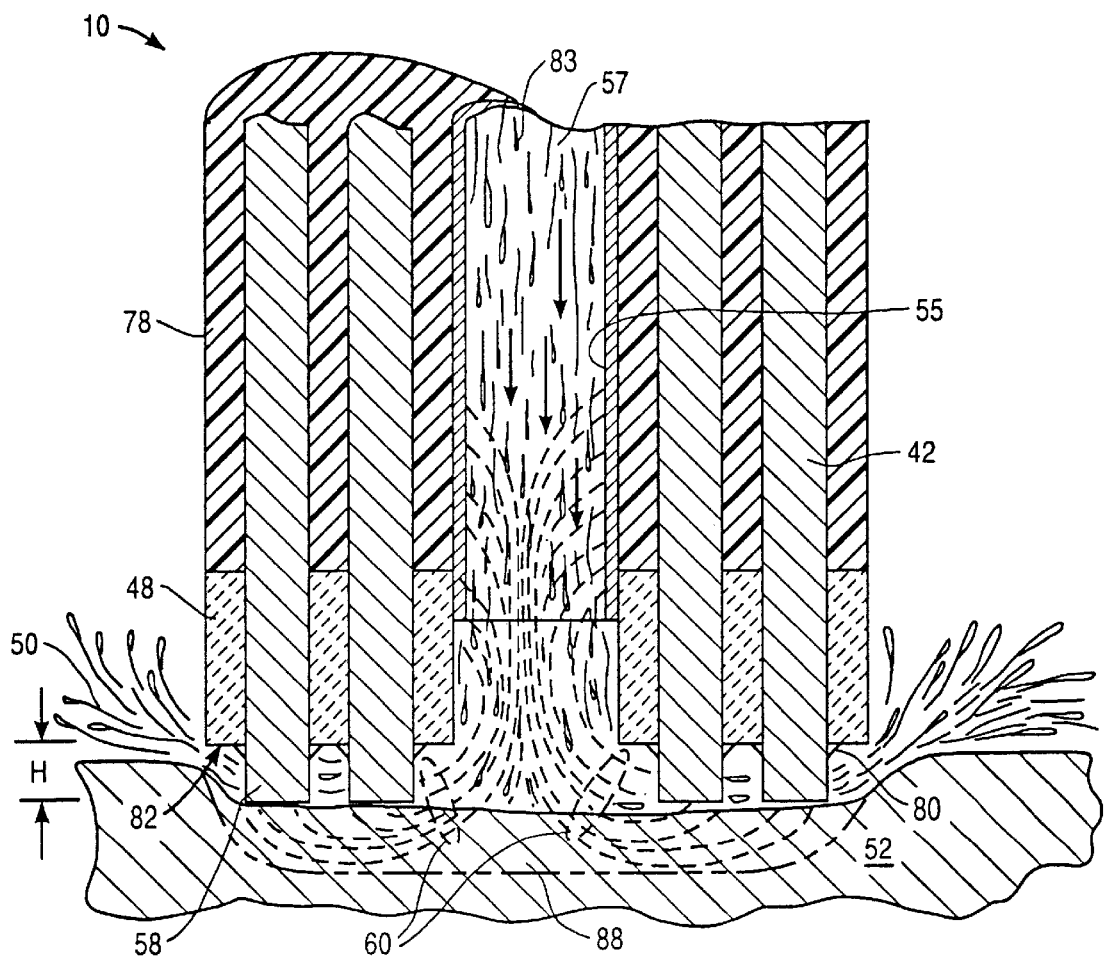
FIG. 3 is a detailed cross-sectional view of an alternative embodiment of the electrosurgical probe of FIG. 1.

As shown in FIG. 2A, the support matrix 48 is adhesively joined to a tubular support member 78 that extends most or all of the distance between matrix 48 and the proximal end of probe 10. Tubular member 78 preferably comprises an electrically insulating material, such as an epoxy, injection moldable plastic or silicone-based material. In a preferred construction technique, electrode terminals 58 extend through pre-formed openings in the support matrix 48 so that they protrude above electrode array surface 82 by the desired distance H (FIG. 3). The electrodes may then be bonded to the distal surface 82 of support matrix 48, typically by an inorganic sealing material 80. Sealing material 80 is selected to provide effective electrical insulation, and good adhesion to both the ceramic matrix 48 and the platinum or titanium electrode terminals. Sealing material 80 additionally should have a compatible thermal expansion coefficient and a melting point well below that of platinum or titanium and alumina or zirconia, typically being a glass or glass ceramic.

In the embodiment shown in FIGS. 2A and 2B, probe 10 includes a return electrode 56 for completing the current path between electrode terminals 58 and power supply 28. Return electrode 56 is preferably an annular member positioned around the exterior of shaft 13 of probe 10. Return electrode 56 may fully or partially circumscribe tubular support member 78 to form an annular gap 54 therebetween for flow of electrically conducting liquid 50 therethrough, as discussed below. Gap 54 preferably has a width in the range of 0.15 mm to 4 mm. Return electrode 56 extends from the proximal end of probe 10, where it is suitably connected to power supply 28 via connectors 19, 20, to a point slightly proximal of electrode array surface 82, typically about 0.5 to 10 mm and more preferably about 1 to 10 mm.

Return electrode 56 is disposed within an electrically insulative jacket 18, which is typically formed as one or more electrically insulative sheaths or coatings, such as polytetrafluoroethylene, polyimide, and the like. The provision of the electrically insulative jacket 18 over return electrode 56 prevents direct electrical contact between return electrode 56 and any adjacent body structure or the surgeon. Such direct electrical contact between a body structure (e.g., tendon) and an exposed common electrode member 56 could result in unwanted heating and necrosis of the structure at the point of contact causing necrosis.

Return electrode 56 is preferably formed from an electrically conductive material, usually metal, which is selected from the group consisting of stainless steel alloys, platinum or its alloys, titanium or its alloys, molybdenum or its alloys, and nickel or its alloys. The return electrode 56 may be composed of the same metal or alloy which forms the electrode terminals 58 to minimize any potential for corrosion or the generation of electrochemical potentials due to the presence of dissimilar metals contained within an electrically conductive fluid 50, such as isotonic saline (discussed in greater detail below).

As shown in FIG. 2A, return electrode 56 is not directly connected to electrode terminals 58. To complete this current path so that terminals 58 are electrically connected to return electrode 56 via target tissue 52, electrically conducting liquid 50 (e.g., isotonic saline) is caused to flow along liquid paths 83. A liquid path 83 is formed by annular gap 54 between outer return electrode 56 and tubular support member 78. An additional liquid path 83 may be formed between an inner lumen 57 within an inner tubular member 59. However, it is generally preferred to form the liquid path 83 near the perimeter of the probe so that the electrically conducting liquid tends to flow radially inward towards the target site 88 (this preferred embodiment is illustrated in FIGS. 8–19). In the embodiment shown in FIGS. 2–5, the liquid flowing through inner lumen 57 may tend to splash radially outward, drawing electrical current therewith and potentially causing damage to the surrounding tissue.

The electrically conducting liquid 50 flowing through fluid paths 83 provides a pathway for electrical current flow between target tissue 52 and return electrode 56, as illustrated by the current flux lines 60 in FIG. 2A. When a voltage difference is applied between electrode array 12 and return electrode 56, high electric field intensities will be generated at the distal tips of terminals 58 with current flow from array 12 through the target tissue to the return electrode, the high electric field intensities causing ablation of tissue 52 in zone 88.

Figure 2C:
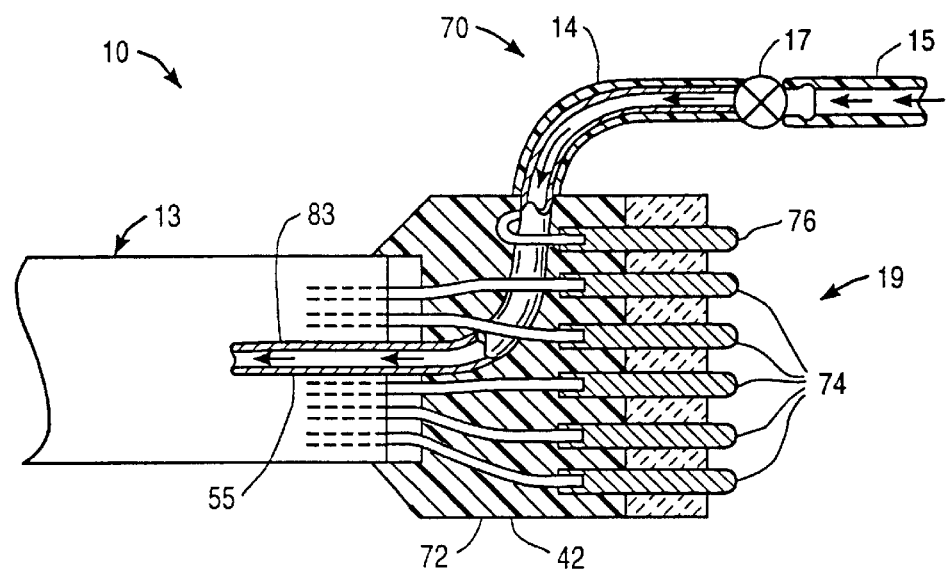
FIG. 2C is a cross-sectional view of the proximal end of the electrosurgical probe, illustrating an arrangement for coupling the probe to the electrically conducting liquid supply of FIG. 1.
Figure 4:
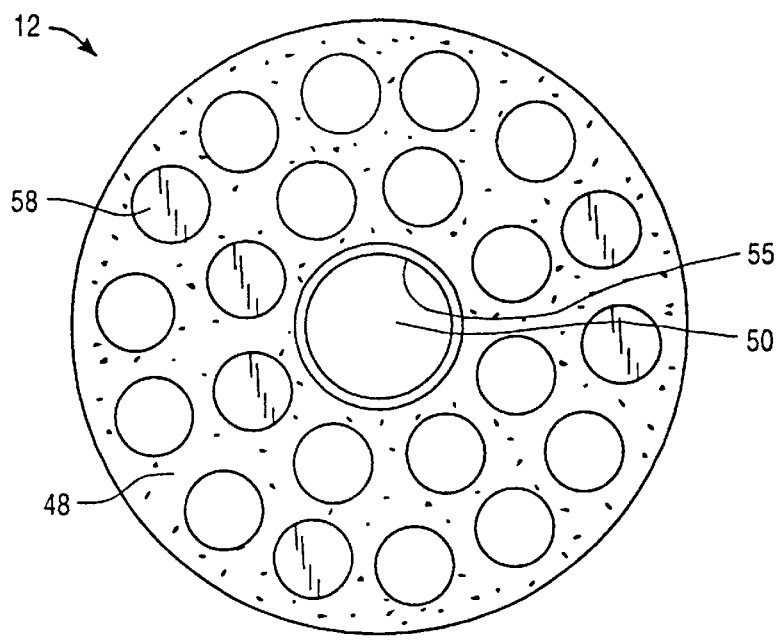
FIG. 4 is an end view of the distal end of the electrosurgical probe of FIG. 3.

FIGS. 2C, 3 and 4 illustrate an alternative embodiment of electrosurgical probe 10 which has a return electrode 55 positioned within tubular member 78. Return electrode 55 is preferably a tubular member defining an inner lumen 57 for allowing electrically conducting liquid 50 (e.g., isotonic saline) to flow therethrough in electrical contact with return electrode 55. In this embodiment, a voltage difference is applied between electrode terminals 58 and return electrode 55 resulting in electrical current flow through the electrically conducting liquid 50 as shown by current flux lines 60 (FIG. 3). As a result of the applied voltage difference and concomitant high electric field intensities at the tips of electrode terminals 58, tissue 52 becomes ablated or transected in zone 88.

FIG. 2C illustrates the proximal or connector end 70 of probe 10 in the embodiment of FIGS. 3 and 4. Connector 19 comprises a plurality of individual connector pins 74 positioned within a housing 72 at the proximal end 70 of probe 10. Electrode terminals 58 and the attached insulating conductors 42 extend proximally to connector pins 74 in connector housing 72. Return electrode 55 extends into housing 72, where it bends radially outward to exit probe 10. As shown in FIGS. 1 and 2C, a liquid supply tube 15 removably couples liquid source 21, (e.g., a bag of fluid elevated above the surgical site or having a pumping device), with return electrode 55. Preferably, an insulating jacket 14 covers the exposed portions of electrode 55. One of the connector pins 76 is electrically connected to return electrode 55 to couple electrode 55 to power supply 28 via cable 34. A manual control valve 17 may also be provided between the proximal end of electrode 55 and supply tube 15 to allow the surgical team to regulate the flow of electrically conducting liquid 50.

Figure 6:
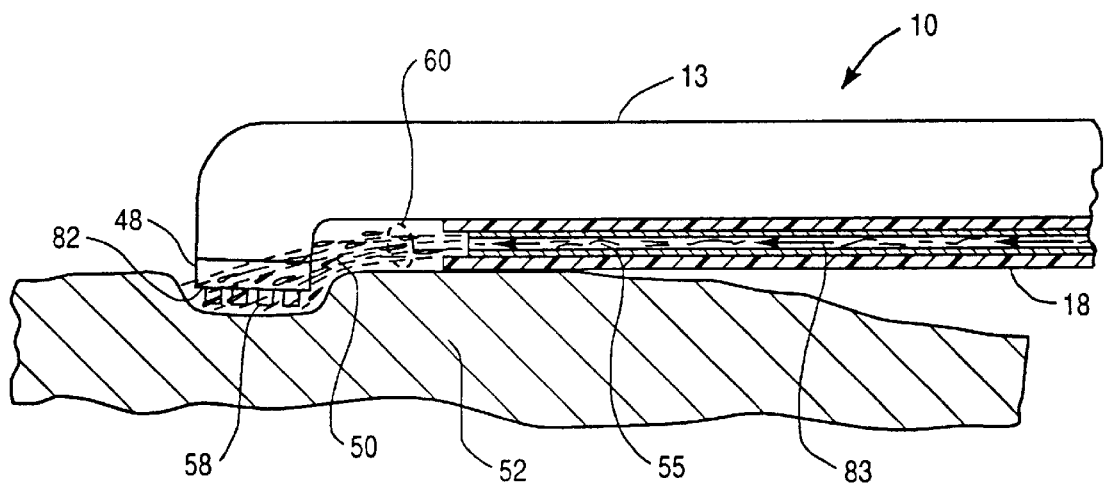
FIG. 6 is a partial cross-sectional side view of a further embodiment of the electrosurgical probe with the electrode array disposed transversely to the axis of the probe.

FIG. 6 illustrates another embodiment of probe 10 where the distal portion of shaft 13 is bent so that electrode terminals extend transversely to the shaft. Preferably, the distal portion of shaft 13 is perpendicular to the rest of the shaft so that electrode array surface 82 is generally parallel to the shaft axis, as shown in FIG. 6. In this embodiment, return electrode 55 is mounted to the outer surface of shaft 13 and is covered with an electrically insulating jacket 18. The electrically conducting fluid 50 flows along flow path 83 through return electrode 55 and exits the distal end of electrode 55 at a point proximal of electrode surface 82. The fluid is directed exterior of shaft to electrode surface 82 to create a return current path from electrode terminals 58, through target tissue 52, to return electrode 55, as shown by current flux lines 60.

Figure 7:
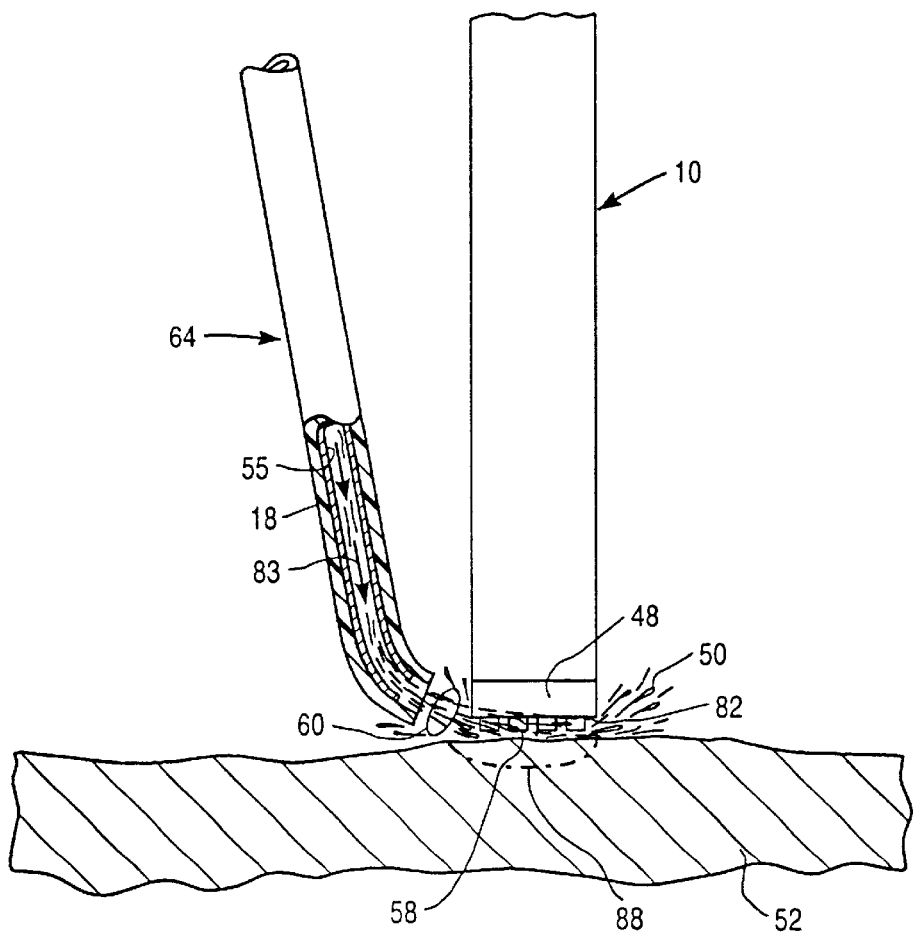
FIG. 7 is a partial front cross-sectional view of an electrosurgical probe and an electrically conductive liquid supply shaft illustrating use of the probe and the shaft in ablating target tissue.

FIG. 7 illustrates another embodiment of the invention where electrosurgical system 11 further includes a liquid supply instrument 64 for supplying electrically conducting fluid 50 between electrode terminals 58 and return electrode 55. Liquid supply instrument 64 comprises an inner tubular member or return electrode 55 surrounded by an electrically insulating jacket 18. Return electrode 55 defines an inner passage 83 for flow of fluid 50. As shown in FIG. 7, the distal portion of instrument 64 is preferably bent so that liquid 50 is discharged at an angle with respect to instrument 64. This allows the surgical team to position liquid supply instrument 64 adjacent electrode surface 82 with the proximal portion of supply instrument 64 oriented at a similar angle to probe 10.

Figure 8:
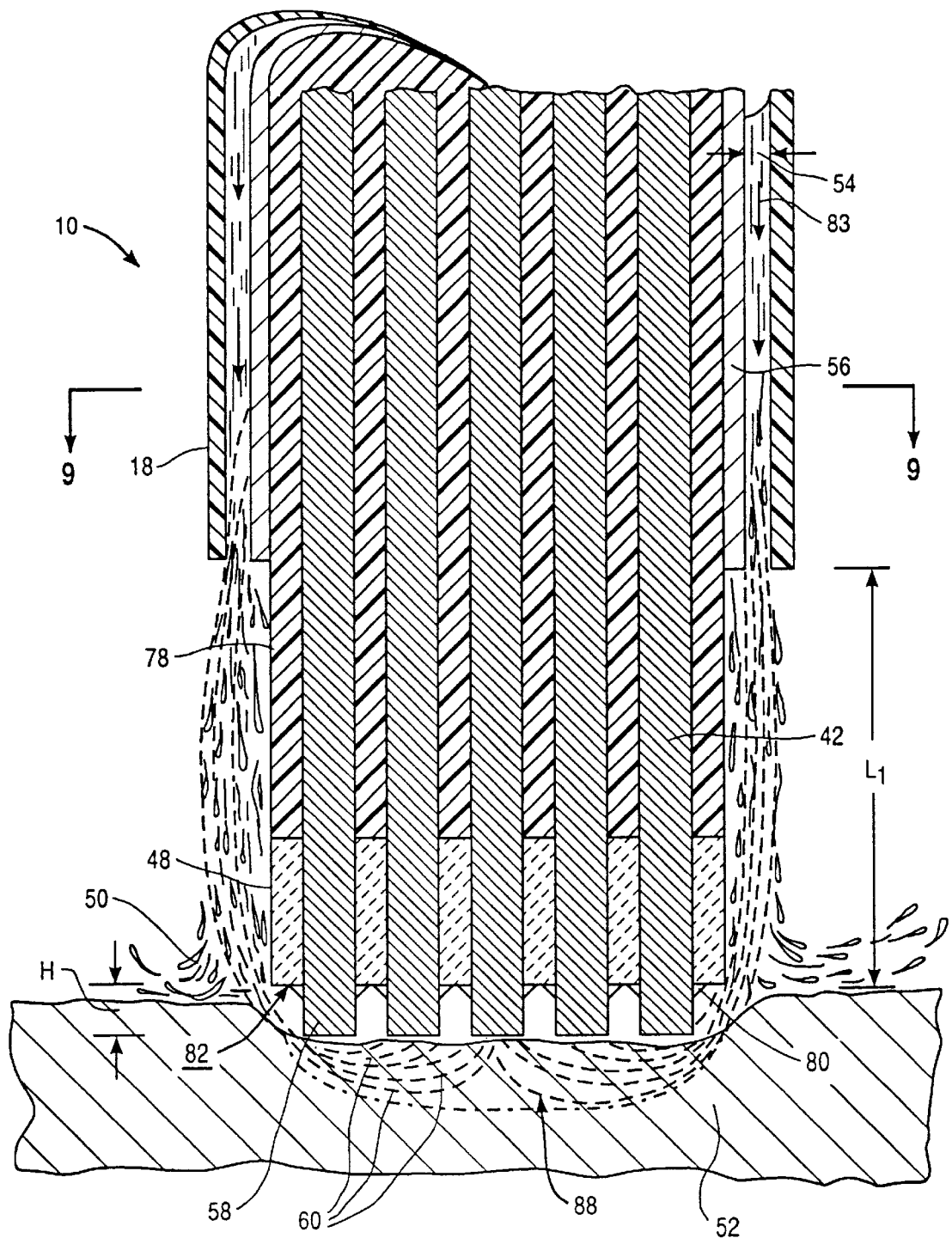
FIG. 8 is an enlarged, cross-sectional view of the distal tip of yet another embodiment of the electrosurgical probe of FIG. 1.
Figure 9:
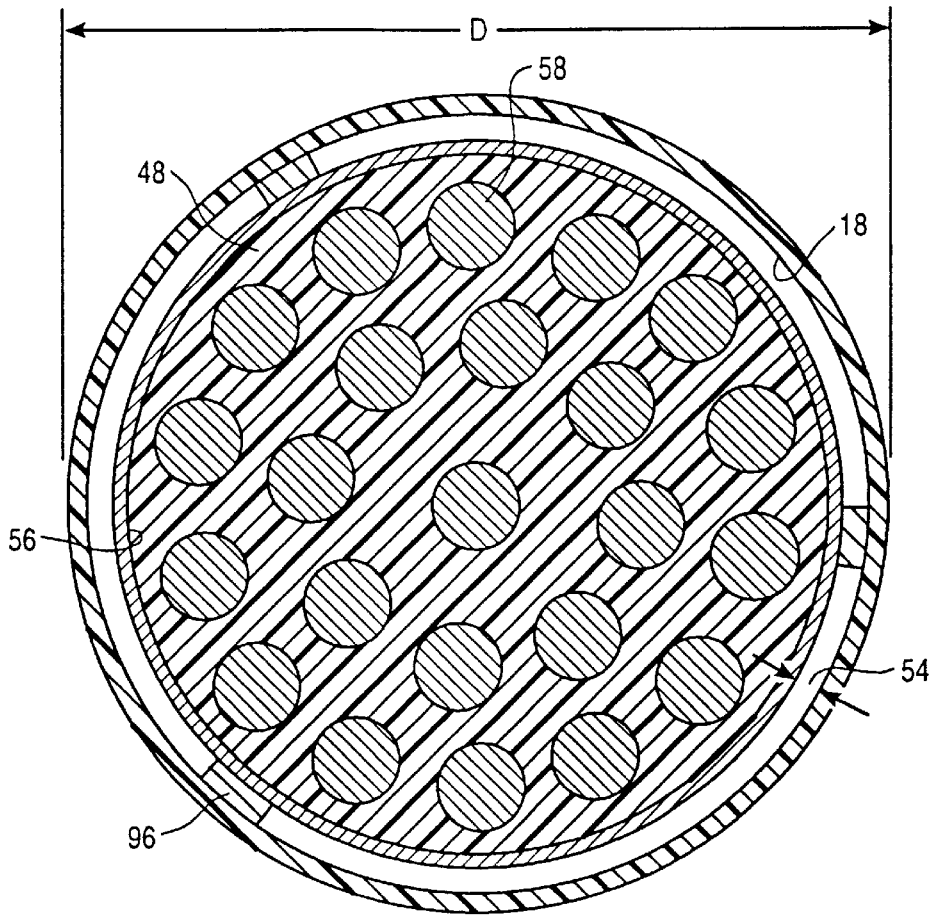
FIG. 9 is a detailed end view of the probe of FIG. 8.
Figure 10:
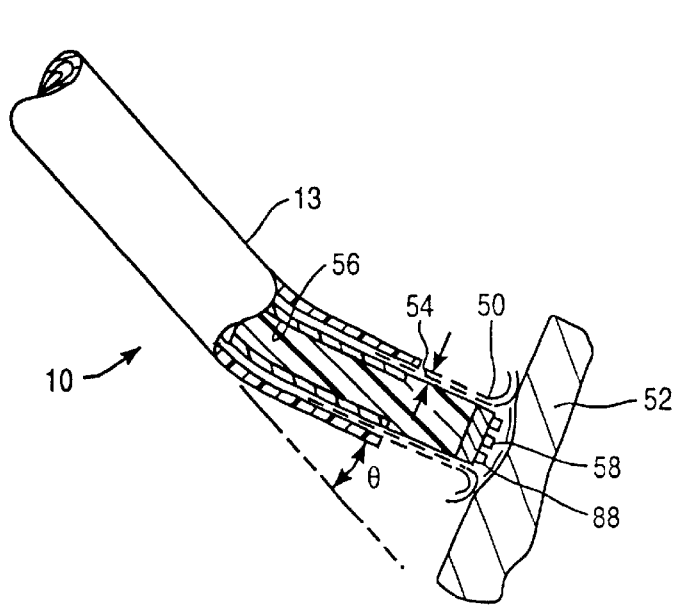
FIG. 10 is a side view of an electrosurgical probe having a shaft with an angled distal portion.
Figure 11:
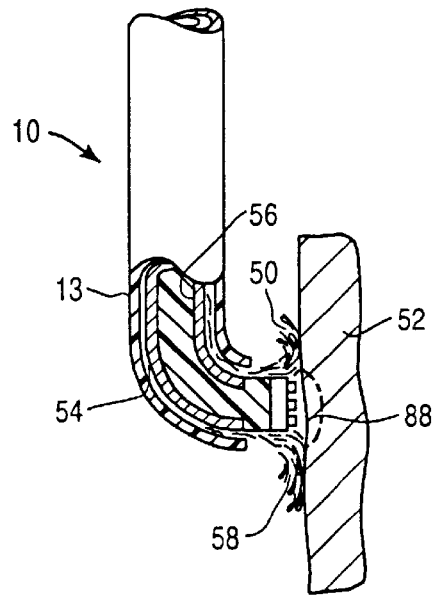
FIG. 11 is a side view of an electrosurgical probe having a shaft with a perpendicular distal portion.

FIGS. 8 and 9 illustrate another embodiment of probe 10 where the return electrode is an outer tubular member 56 that circumscribes support member 78 and conductors 42. Insulating jacket 18 surrounds tubular member 56 and is spaced from member 56 by a plurality of longitudinal ribs 96 to define an annular gap 54 therebetween (FIG. 9). Annular gap preferably has a width in the range of 0.15 mm to 4 mm. Ribs 96 can be formed on either the jacket 18 or member 56. The distal end of return electrode 56 is a distance $L_1$ from electrode support surface 82. Distance $L_1$ is preferably about 0.5 to 10 mm and more preferably about 1 to 10 mm. The length $L_1$ of return electrode 56 will generally depend on the electrical conductivity of the irrigant solution.

As shown in FIG. 8, electrically conducting liquid 50 flows through annular gap 54 (in electrical communication with the return electrode) and is discharged through the distal end of gap 54. The liquid 50 is then directed around support member 78 to electrode terminals 58 to provide the current pathway between the electrode terminals and return electrode 56. Since return electrode 56 is proximally recessed with respect to electrode surface 82, contact between the return electrode 56 and surrounding tissue is minimized. In addition, the distance $L_1$ between the active electrode terminals 58 and the return electrode 56 reduces the risk of current shorting therebetween.

The present invention is not limited to an electrode array disposed on a relatively planar surface at the distal tip of probe 10, as described above. Referring to FIGS. 12–14, an alternative probe 10 includes a pair of electrodes 58*a*, 58*b* mounted to the distal end of shaft 13. Electrodes 58*a*, 58*b* are electrically connected to power supply as described above and preferably have tips 100*a*, 100*b* with a screwdriver or flattened shape. The screwdriver shape provides a greater amount of "edges" to electrodes 58*a*, 58*b*, to increase the electric field intensity and current density at the edges and thereby improve the cutting ability as well as the ability to limit bleeding from the incised tissue (i.e., hemostasis).

As shown in FIG. 12, current flows between electrode tips 100*a* and 100*b* as indicated by current flux lines 60 to heat the target tissue 52. The surgeon then moves probe 10 transversely across tissue 52 to effect an incision 102 in tissue 52, as shown in FIG. 14.

Other modifications and variations can be made to disclose embodiments without departing from the subject invention as defined in the following claims. For example, shaft 13 of probe 10 may have a variety of configurations other than the generally linear shape shown in FIGS. 1–8. For example, shaft 13 may have a distal portion that is angled, in the range of 10° to 30° (FIG. 10) or 90° (FIGS. 11 and 6), to improve access to the operative site of the tissue 52 being ablated or cut (see FIG. 10). A shaft having a 90° bend angle may be particular useful for accessing gingiva located in the back portion of the patient's mouth and a shaft having a 10° to 30° bend angle may be useful for accessing gingiva near or in the front of the patient's mouth.

In addition, it should be noted that the invention is not limited to an electrode array comprising a plurality of active electrodes. The invention could utilize a plurality of return electrodes, e.g., in a bipolar array or the like. In addition, depending on other conditions, such as the peak-to-peak voltage, electrode diameter, etc., a single active electrode may be sufficient to develop a vapor layer and induce the discharge of energy to ablate or cut tissue, as described above.

Figure 21:
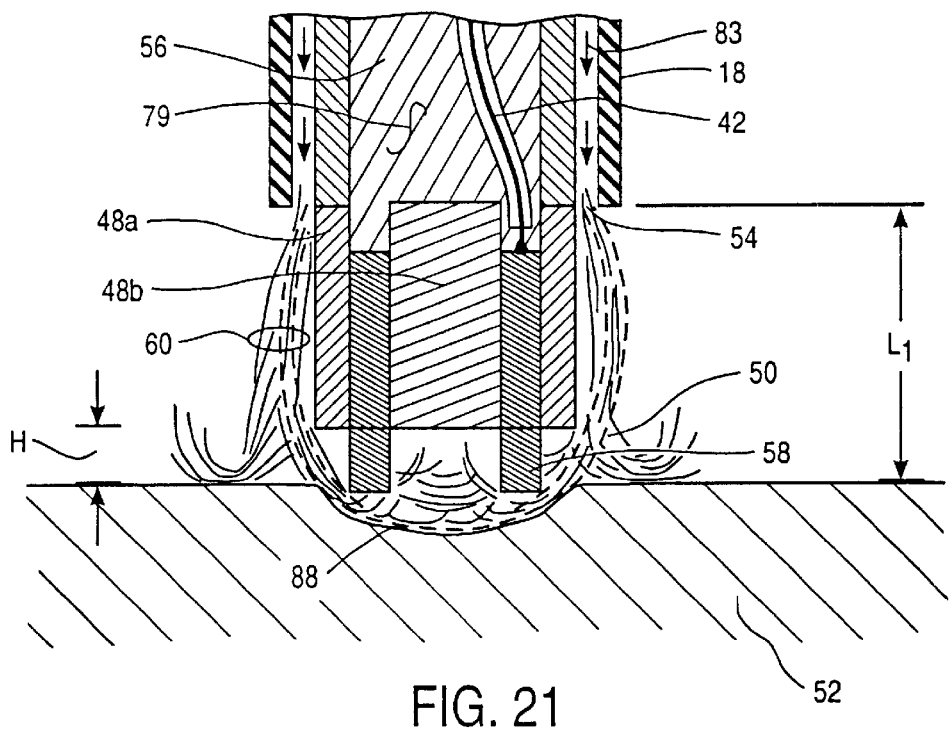
FIG. 21 depicts a distal portion of an alternative embodiment of the probe of FIGS. 2A–2C incorporating a single electrode with a tubular geometry.
Figure 22:
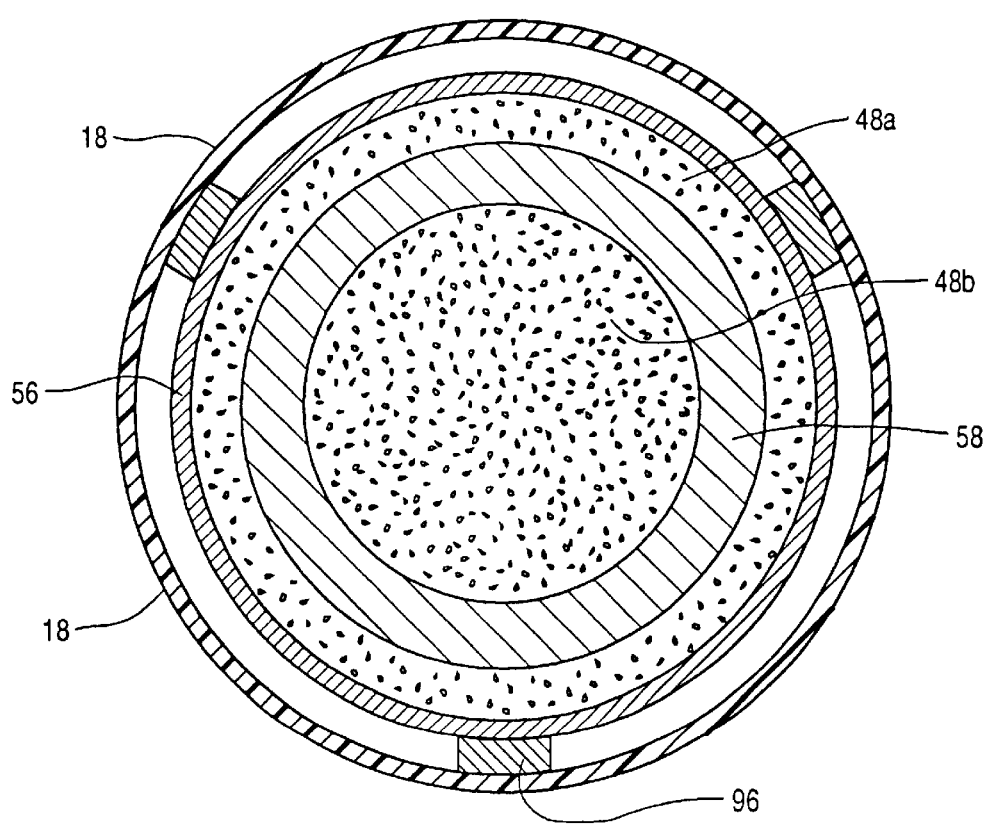
FIG. 22 is a cross-sectional view of the distal end of the probe of FIG. 21.

By way of example, FIGS. 21 and 22 illustrate the design of a probe 10 according to the present invention comprising a single active electrode 58 having a tubular geometry. As described above, the return electrode may be an outer tubular member 56 that circumscribes insulated conductor 42 and adhesive bonding material 79 which, in turn, adhesively joins to active electrode support members 48*a* and 48*b*. Electrode support members 48*a* and 48*b* may be ceramic, glass ceramic or other electrically insulating material which resists carbon or arc tracking. A preferred electrode support member material is alumina. In the example embodiment, a solid rod of alumina forms an inner portion 48*b* of electrode support member 48 and a hollow tube of alumina forms an outer portion 48*a* of electrode support member 48. Tubular shaped active electrode 58 may be fabricated using shaped cylinder of this metal comprising an electrically conductive metal, such as platinum, tantalum, tungsten, molybdenum, columbium or alloys thereof. Active electrode 58 is connected to connector 19 (see FIG. 2C) via an insulated lead 108. An electrically insulating jacket 18 surrounds tubular member 56 and may be spaced from member 56 by a plurality of longitudinal ribs 96 to define an annular gap 54 therebetween (FIG. 22). Annular gap 54 preferably has a width in the range of 0.15 to 4 mm. Ribs 96 can be formed on either jacket 18 or tubular member 56. The distal end of the return electrode 56 is a distance $L_1$ from electrode support surface 82. Distance $L_1$ is preferably about 0.5 mm to 10 mm and more preferably about 1 to 10 mm. The length $L_1$ of return electrode 56 will generally depend on the electrical conductivity of the irrigant solution.

As shown in FIG. 21, electrically conducting liquid 50 flows through annular gap 54 (in electrical communication with return electrode 56) and is discharged through the distal end of gap 54. The liquid 50 is then directed around electrode support member 48*a* to electrode terminal 58 to provide the current pathway between electrode terminal 58 and return electrode 56. As described above, the active and return electrodes are connected to voltage supply 28 via cable 34 (see FIG. 1).

Figure 23:
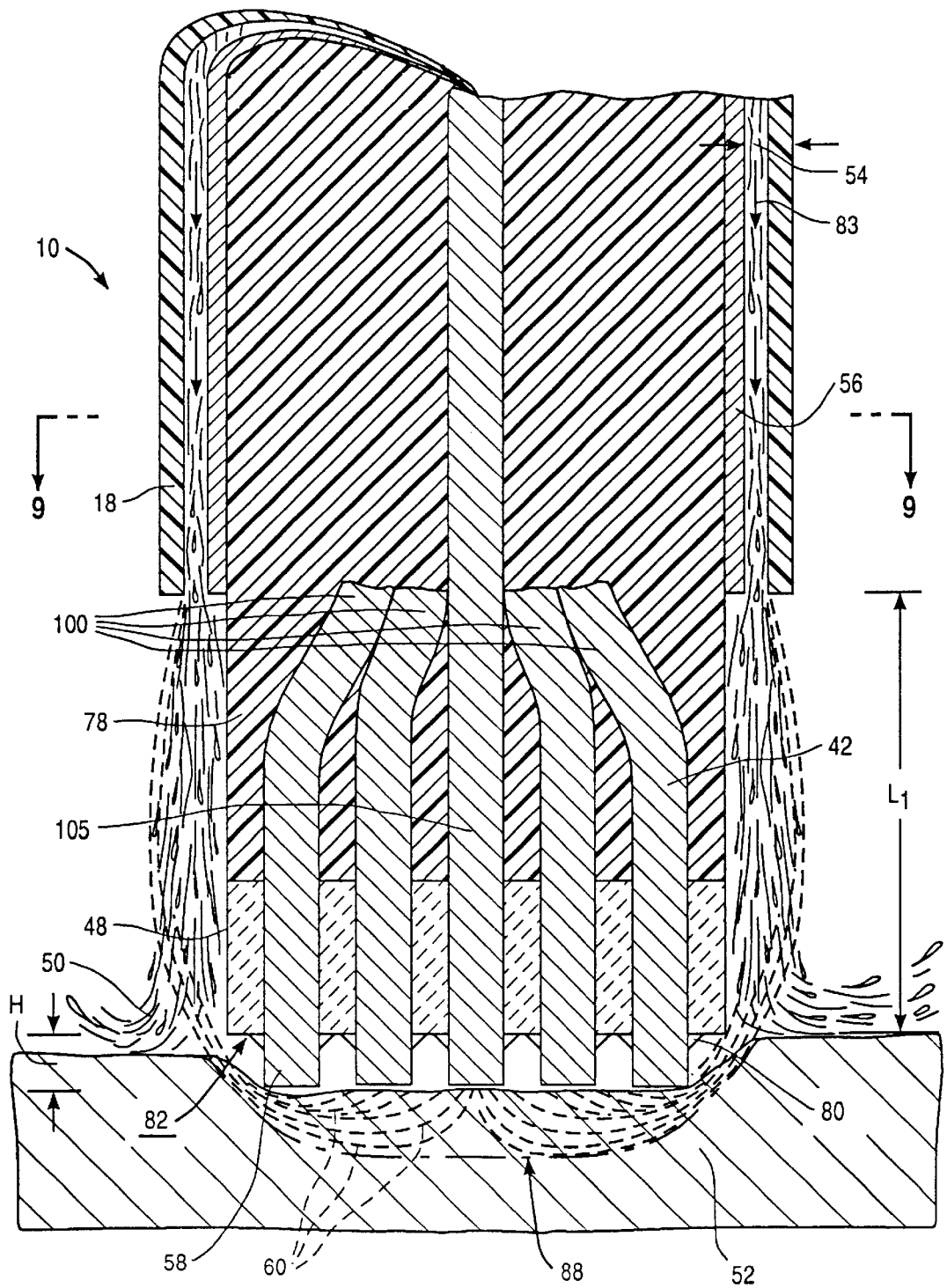
FIG. 23 is a side cross-sectional view of a distal portion of a further embodiment of the probe of FIGS. 2A–2C incorporating a multiplicity of electrodes which converge to a single electrode lead.
Figure 24:
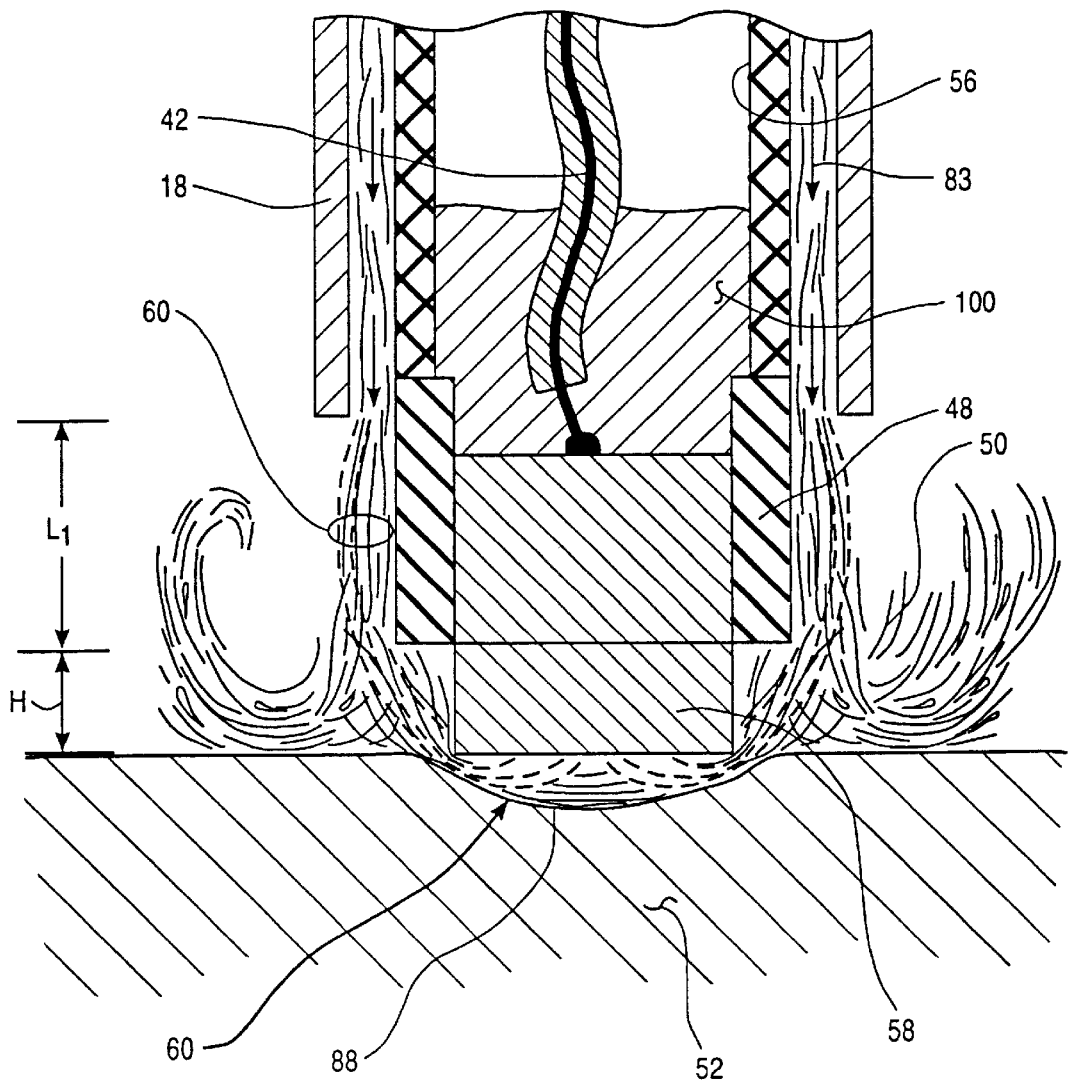
FIG. 24 is a side cross-sectional view of a distal portion of yet another embodiment of the probe of FIGS. 2A–2C incorporating a single electrode connected to a single electrode lead.

FIGS. 23 and 24 illustrate further embodiments of electrosurgical probes according to the present invention. In FIG. 23, a probe 10 comprises a multiplicity of electrodes 58 which converge to a single electrode lead 42. As shown, a central electrode 105 extends to the proximal end of the probe shaft for connection to connector 19 (FIG. 2C). The remainder of the electrodes 58 extend through a portion of the probe shaft and are electrically coupled to central electrode 105 by, for example, a weld, solder joint or crimp connection 100. In FIG. 24, an electrosurgical probe 10 comprises a single electrode 58 connected to a single electrode lead 42. As described above, the active and return electrodes are connected to voltage supply 28 via cable 34 (see FIG. 1).

Both of the single active electrode configurations depicted in FIGS. 21–24 may be used with the integral supply means and return electrodes described above in FIGS. 2–11, 30 and 31. Alternatively, these probe configurations may be operated in body cavities already containing an electrically conducting liquid 50, obviating the need for either an integral supply of said liquid or an electrically insulating sleeve to form a conduit for supply of the electrically conducting liquid 50. Instead, an electrically insulating covering would be applied to substantially all of the return electrode 56 (other than the proximal portion).

Figure 15:
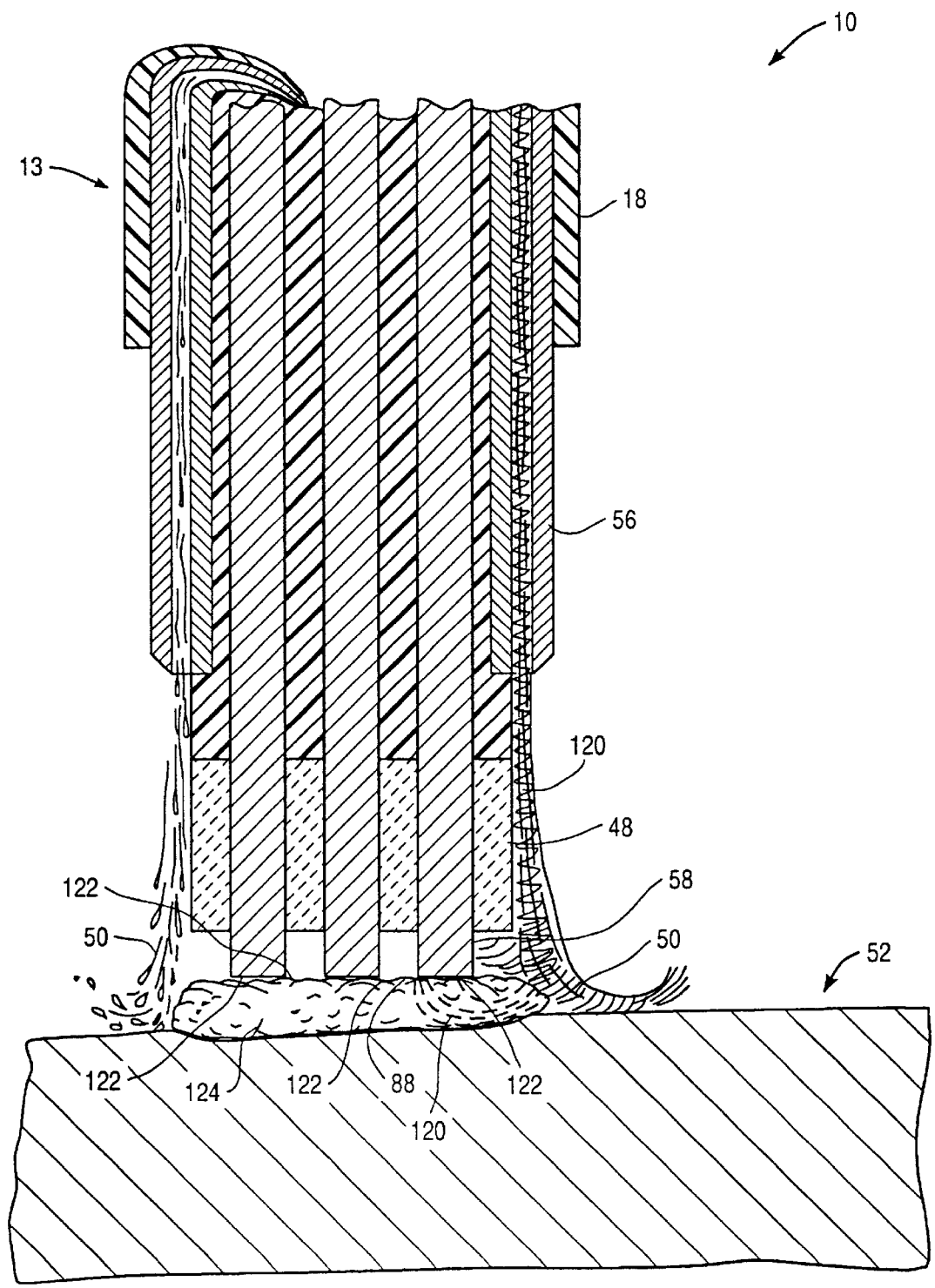
FIG. 15 is a cross-sectional view of the distal tip of the electrosurgical probe, illustrating electric field lines between the active and return electrodes.
Figure 16:
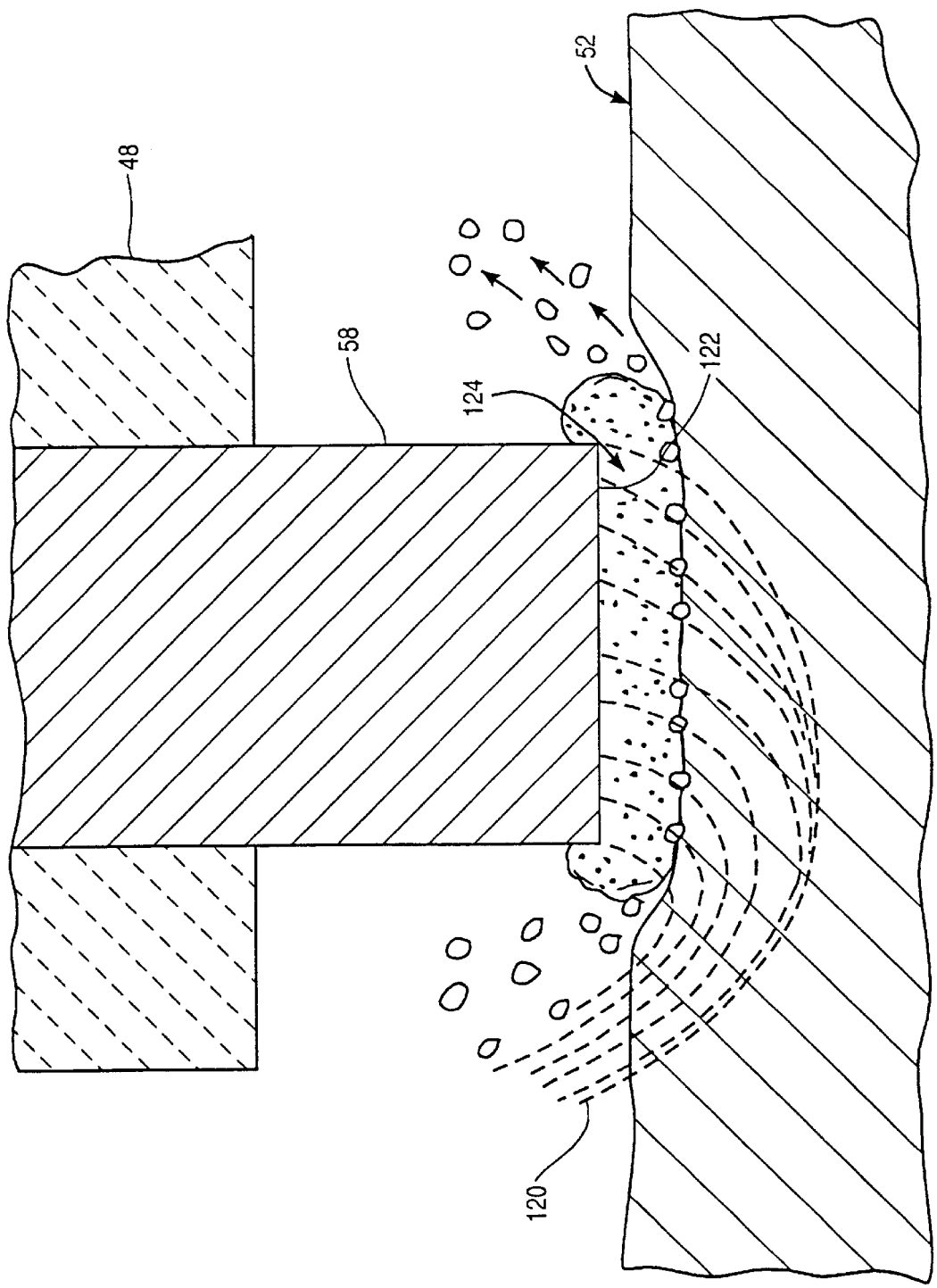
FIG. 16 is an enlarged cross-sectional view of the distal tip of the probe of FIG. 15, illustrating a vapor layer formed between the active electrodes and the target tissue.

FIG. 15 illustrates the current flux lines associated with an electric field 120 applied between the active and return electrodes 56, 58 when a voltage is applied therebetween. As shown, the electric field intensity is substantially higher in the region 88 at the tip of the electrode 58 because the current flux lines are concentrated in these regions. This high electric field intensity leads to induced molecular breakdown of the target tissue through molecular dissociation. Preferably, the electric field intensity is sufficient to ionize the vaporized electrically conducting liquid 50 in a thin layer 124 between the distal tip 122 of the active electrode 58 and the target tissue 52, as shown in FIG. 16. The vapor layer 124 will usually have a thickness of about 0.02 to 2.0 mm.

As shown in FIG. 16, the electric field ionizes the vapor layer due to the presence of an ionizable species (e.g., sodium) within the vapor layer to create a plasma. This ionization, under optimal conditions, induces the discharge of highly energetic electrons and/or photons from the vapor layer. The photon and/or the energetic electrons cause disintegration of the tissue molecules adjacent to the vapor layer. FIG. 16 illustrates the issuance of bubbles 126 of non-condensible gaseous products resulting from the disintegration of tissue at the target site.

The system and method of the present invention is also useful in dermatological procedures, i.e., surface tissue ablation on the patient's outer skin or epidermis. For example, the probe of the present invention can be used for the removal of tissue abnormalities, pigmentations, such as freckles, tattoos, age or liver spots, birth marks, malignant melanomas, and superficial lentigines in the epidermis, and other unwanted tissue, such as soft fatty tissue, cutaneous angiodysplasia, e.g., skin angioma, malignant tumor tissue, lumbago (i.e., tissue bulges extending from the vertebrae) or the like. In addition, the probe of the present invention may be used for removing surface layers of the epidermis to provide younger looking skin (tissue rejuvenation) or for incising, dividing and resecting tissue during cosmetic surgery procedures.

Figure 17:
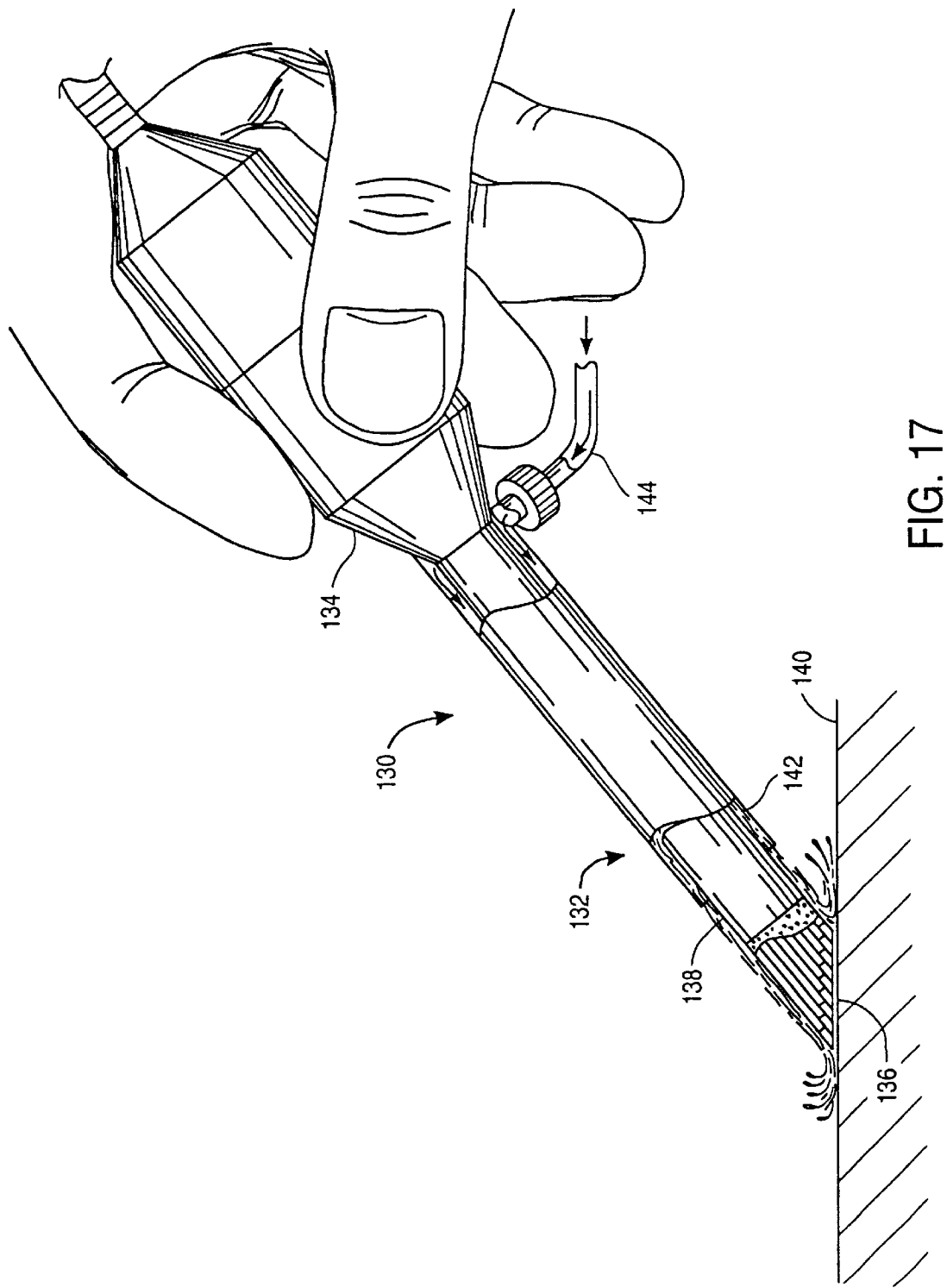
FIG. 17 is a cross-sectional view of an alternative electrosurgical probe for applying high frequency voltage to epidermal tissue layers.

FIG. 17 illustrates an exemplary embodiment, where an electrosurgical probe 130 is utilized to remove the surface layers of the epidermis 140. Probe 130 includes a shaft 132 coupled to a proximal handle 134 for holding and controlling shaft 132. Similar to previous embodiments, probe 130 includes an active electrode array 136 at the distal tip of shaft 132, an annular return electrode 138 extending through shaft 132 and proximally recessed from the active electrode array 136 and an annular lumen 142 between return electrode 138 and an outer insulating sheath 144. Probe 130 further includes a liquid supply conduit 146 attached to handle 134 and in fluid communication with lumen 142 and a source of electrically conducting fluid (not shown) for delivering the fluid past return electrode 138 to the target site on the epidermis 140. As discussed above, electrode array 136 is preferably flush with the distal end of shaft 132 or distally extended from the distal end by a small distance (on the order of 0.005 inches) so to minimize the depth of ablation. Preferably, the distal end of shaft 132 is beveled to improve access and control of probe 130 while treating the epidermal tissue.

The voltage will preferably be sufficient to establish high electric field intensities between the active electrode array 136 and the epidermal tissue 140 to thereby induce molecular breakdown or disintegration of several cell layers of the epidermal tissue. As described above, a sufficient voltage will be applied to develop a thin layer of vapor within the electrically conducting fluid and to ionize the vaporized layer or region between the active electrode(s) and the target tissue. Energy in the form of photons and/or energetic electrons are discharged from the vapor layer to ablate the epidermal tissue, thereby minimizing necrosis of surrounding tissue and underlying cell layers, such as cell structures in the stratum lucidium and/or stratum granulosum.

Figure 18:
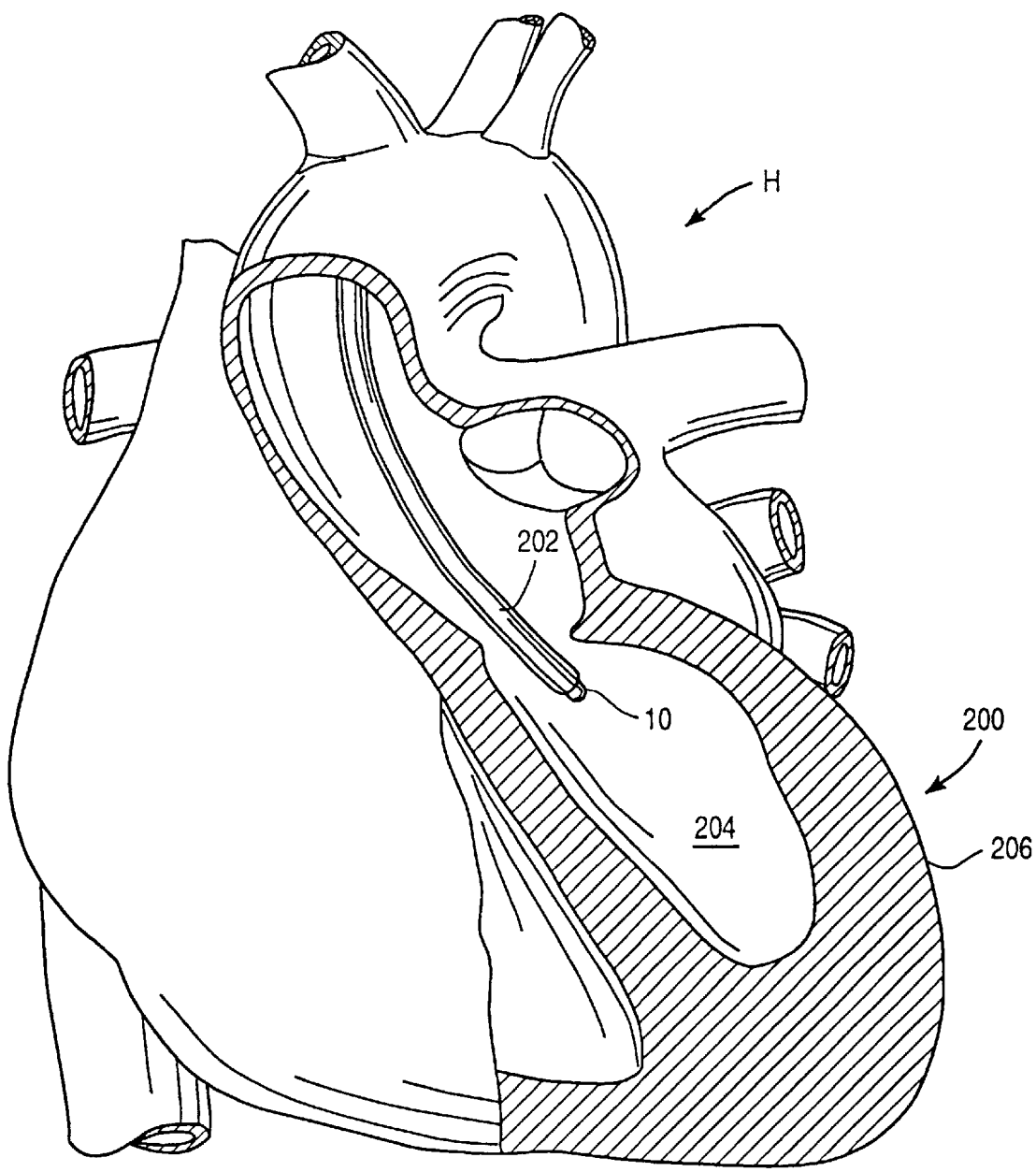
FIG. 18 is a sectional view of the human heart, illustrating the electrosurgical probe within the ventricular cavity for performing a transmyocardial revascularization procedure.
Figure 19:
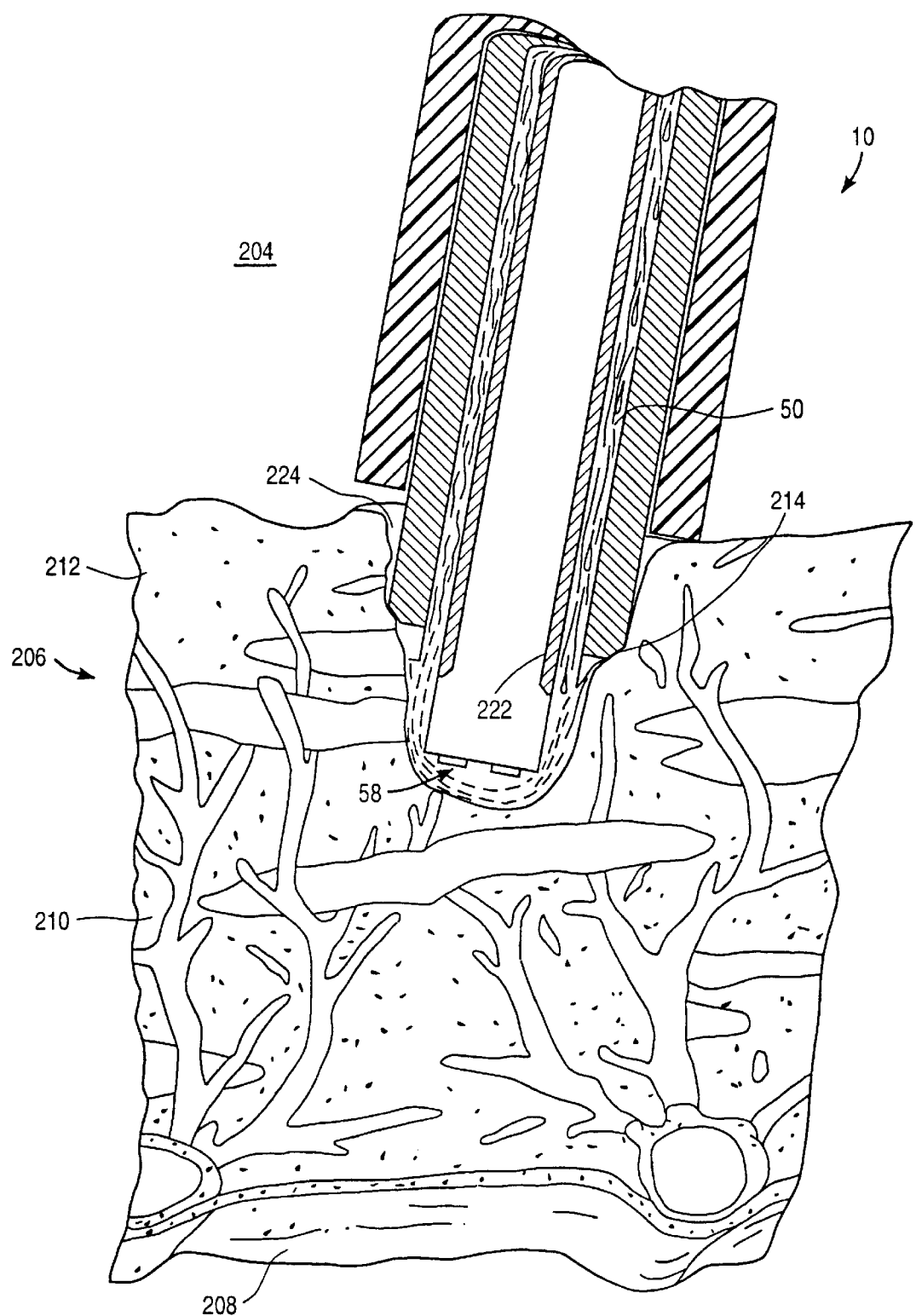
FIG. 19 is a cross-sectional view of the probe boring a channel through the ventricular wall.
Figure 20:
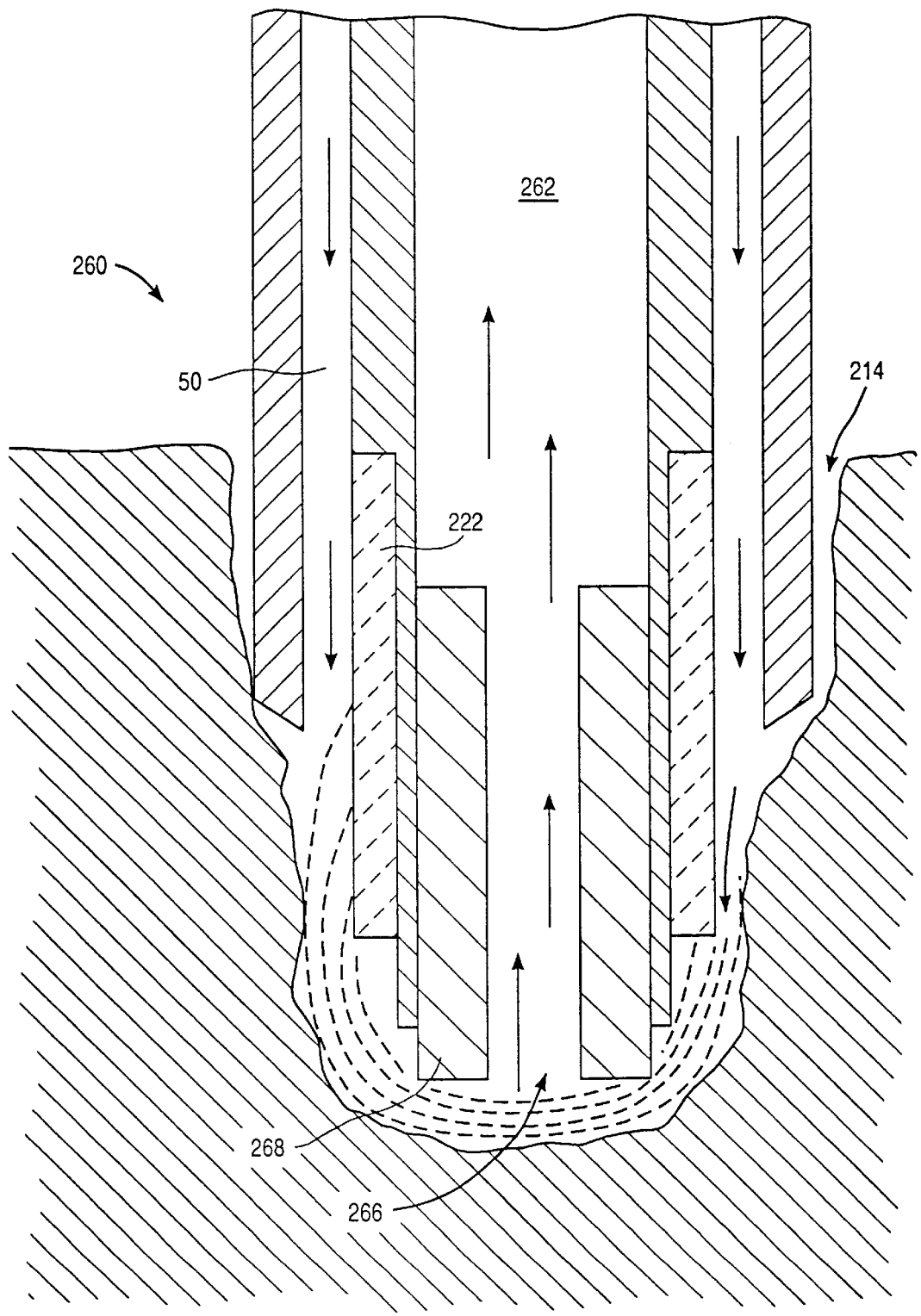
FIG. 20 depicts an alternative embodiment of the probe of FIG. 19 having an inner lumen for aspirating fluid and gases from the transmyocardial channel.

FIGS. 18–20 illustrate an exemplary embodiment of another important application of the present invention. As discussed above, the probe of the present invention may be particularly useful for boring a channel through tissue by axially translating the probe towards the tissue as the tissue is disintegrated by the mechanisms discussed above. In the exemplary embodiment, the probe of the present invention is used in a transmyocardial revascularization procedure to form channels from the myocardium to the ventricular cavity to perfuse the myocardium. This procedure is an alternative to coronary artery bypass surgery for treating coronary artery disease. The channels allow oxygen enriched blood flowing into the ventricular cavity from the aorta to directly flow into the myocardium; rather than exiting the heart and then flowing back into the myocardium through the coronary arteries.

As shown in FIG. 18, electrosurgical probe 10 is positioned into one of the ventricular cavities of the heart, in this case, the right ventricle 200. Electrosurgical probe 10 may be introduced into the right ventricle 200 in a variety of procedures that are well known in the art, such as a thoracotomy, sternotomy or minimally invasive procedures. In the representative embodiment, probe 10 is introduced into the vasculature of the patient through a percutaneous penetration and axially translated via a guide catheter 202 through one of the major vessels to the right ventricular cavity 204. A preferred embodiment incorporates a steerable guide catheter 202 which can be externally controlled by the surgeon to direct the distal portion of the guide catheter 202 and probe 10 to the target site(s) in ventricular cavity 204.

Referring to FIG. 19, ventricle wall 206 comprises an epicardium 208, a myocardium 210 and an endocardium 212. In the representative embodiment, probe 10 will form a channel 214 or artificial vessel from the ventricular cavity 206, through the endocardium 212 and into the myocardium 210 to thereby increase myocardial blood flow from the endocardium 212 to the myocardium 210. The location of channel 214 may be selected based on familiar epicardial anatomic landmarks, such as the epicardial branches of the coronary arteries. Guide catheter 202 is positioned adjacent the inner endocardial wall and probe 10 is axially translated so that the active electrode 58 at its distal end is positioned proximate the heart tissue. In this embodiment, the probe includes a single, annular electrode 58 at its distal tip for ablation of the heart tissue. However, it will be readily recognized that the probe may include an array of electrode terminals as described in detail above.

Electrically conducting liquid 50 is delivered through an annular lumen 220 between an annular return electrode 222 and an insulating sheath 224 of the probe. Return electrode 222 is recessed from the distal end of active electrode 58, preferably about 0.025 to 0.050 inches. Alternatively, the return electrode may be positioned on the exterior surface (skin) of the patient, or it may be located nearby on a more proximal position of the probe. Similar to the above embodiments, a high frequency voltage (e.g., 100 kHz) is applied between active electrode(s) 58 and return electrode 222 to establish a current flow therebetween that ablates or disintegrates the heart tissue. The high frequency voltage will preferably be sufficient to vaporize a thin layer of the electrically conducting liquid and to induce the discharge of photon and/or electron energy from the vapor layer to provide cold ablation of the heart tissue.

Ablation of the tissue may be facilitated by axially reciprocating and/or rotating the probe within guide catheter 202 a distance of between about 0.05 to 0.20 inches. This axial reciprocation or rotation allows the electrically conducting liquid 50 to flow over the tissue surface being canalized, thereby cooling this tissue and preventing significant thermal damage to the surrounding tissue cells.

FIG. 20 illustrates an alternative embodiment of the probe of FIG. 1. In this embodiment, the probe 260 includes a central lumen 262 having a proximal end attached to a suitable vacuum source (not shown) and an open distal end 266 for aspirating the target site. The active electrode is preferably a single annular electrode 268 surrounding the open distal end 266 of central lumen 262. Central lumen 262 is utilized to remove the ablation products (e.g., liquids and gases) generated at the target site and excess electrically conductive irrigant during the procedure.

In both of the above embodiments, the present invention provides localized ablation or disintegration of heart tissue to form a revascularization channel 214 of controlled diameter and depth. Usually, the diameter will be in the range of 0.5 mm to 3 mm. Preferably, the radio frequency voltage will be in the range of 400 to 1400 volts peak-to-peak to provide controlled rates of tissue ablation and hemostasis while minimizing the depth of necrosis of tissue surrounding the desired channel. This voltage will typically be applied continuously throughout the procedure until the desired length of the channel 214 is completely formed. However, the heartbeat may be monitored and the voltage applied in pulses that are suitably timed with the contractions (systole) of the heart.

It should be noted that the above embodiment is merely representative and is not intended to limit the invention. For example, the electrosurgical probe can be used to effect a myocardial revascularization channel from the exterior of the heart into the ventricular cavity. In this procedure, the probe will be introduced into the thoracic cavity and positioned adjacent the epicardial layer of one of the ventricular walls via one of a variety of conventional manners. The above electrosurgical procedure will then be performed as the electrode is translated towards the heart until a channel is formed to the ventricular cavity.

The system and method of the present invention may also be useful to efficaciously ablate (i.e., disintegrate) cancer cells and tissue containing cancer cells, such as cancer on the surface of the epidermis, eye, colon, bladder, cervix, uterus and the like. The present invention's ability to completely disintegrate the target tissue can be advantageous in this application because simply vaporizing cancerous tissue may lead to spreading of viable cancer cells (i.e., seeding) to other portions of the patient's body or to the surgical team in close proximity to the target tissue. In addition, the cancerous tissue can be removed to a precise depth while minimizing necrosis of the underlying tissue.

Figure 25:
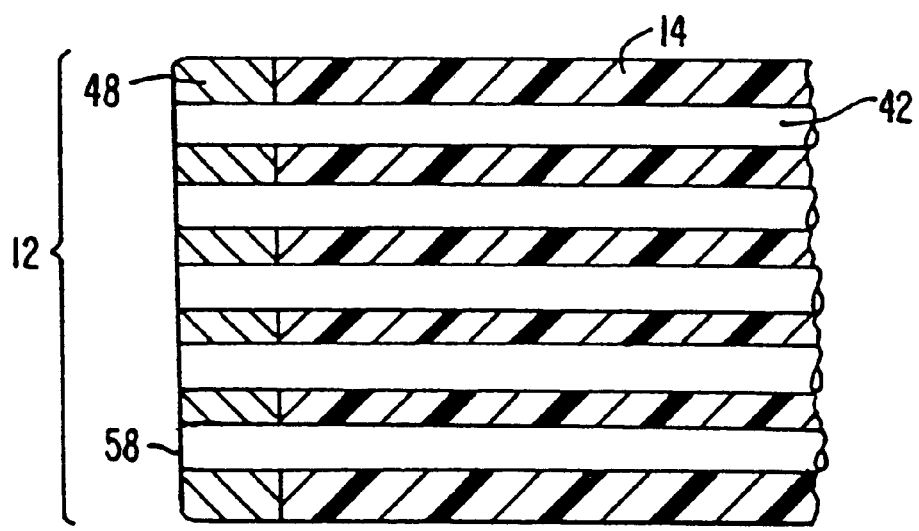
FIG. 25 is a detailed cross-section view of the distal end of an electrosurgical probe illustrating an electrode arrangement suitable for smoothing of tissue structures.

Referring to FIG. 25 another embodiment of the present invention intended for smoothing of body structures (e.g., articular cartilage located on the surface of a condyle) while minimizing the depth of necrosis of the underlying tissue includes electrode terminals 58 in an electrical insulating matrix 48 is similar to the array shown previously except that the electrode terminals 58 are flush with the surface of the electrically insulating matrix 48. The rate of ablation achievable with the use of "flush" electrode terminals 58 is lower than that for electrodes which extend beyond the face of the electrically insulative matrix 48, but such flush electrode structure can provide a smoother surface on the body structure being treated while minimizing the depth of ablation and necrosis.

What is claimed is:

1. A method for smoothing body structures comprising:

positioning an electrode terminal into at least close proximity with a target surface of a body structure at a target site in the presence of an electrically conductive fluid;

positioning a return electrode in close proximity to the body structure such that the return electrode is not in contact with said target surface;

applying high frequency voltage to the electrode terminal and the return electrode such that an electrical current flows from the electrode terminal, through the target site, and to the return electrode; and smoothing the target surface of the body structure with the high frequency voltage.

2. The method of claim 1 wherein the body structure comprises articular cartilage on the surface of a condyle, the method comprising smoothing an irregular surface of the articular cartilage.

3. The method of claim 2 wherein the voltage is sufficient to smooth the irregular surface of the articular cartilage while minimizing the depth of ablation and necrosis in the articular cartilage.

4. The method of claim 2 further comprising providing sufficient voltage to the electrode terminal to ablate at least a portion of cartilage strands on the irregular surface of the articular cartilage to smooth said surface.

5. The method of claim 2 further comprising providing sufficient voltage to the electrode terminal to heat at least a portion of cartilage strands on the irregular surface of the articular cartilage to smooth said surface.

6. The method of claim 2 further comprising providing sufficient voltage to the electrode terminal to thermally soften at least a portion of the irregular surface of the articular cartilage to smooth said surface.

7. The method of claim 1 further comprising positioning the return electrode within the electrically conductive fluid to generate a current flow path between the electrode terminal and the return electrode.

8. The method of claim 7 further comprising immersing the target site within a volume of the electrically conductive fluid and positioning the return electrode within the volume of electrically conductive fluid to generate the current flow path between the target site and the return electrode.

9. The method of claim 8 wherein the electrically conductive fluid has originated from an external source outside of the patient's body.

10. The method of claim 8 wherein the electrically conductive fluid comprises isotonic saline.

11. The method of claim 1 wherein the electrical current flows substantially through the electrically conductive fluid while minimizing electrical current flow passing through the body structure.

12. The method of claim 1 wherein at least a portion of the electrical current passes through the body structure.

13. The method of claim 1 wherein the electrode terminal comprises a single electrode disposed near the distal end of an instrument shaft.

14. The method of claim 1 wherein the electrode terminal includes an array of electrically isolated electrode terminals disposed near the distal end of an instrument shaft.

15. The method of claim 13 including independently controlling current flow from at least two electrode terminals based on electrical impedance between each electrode terminal and the return electrode.

16. The method of claim 1 wherein the return electrode is spaced from the electrode terminal such that when the electrode terminal is brought adjacent a tissue structure immersed in electrically conductive fluid, the return electrode is spaced from the tissue structure and the electrically conductive fluid completes a conduction path between the electrode terminal and the return electrode.

17. The method of claim 16 further comprising moving the electrode terminal transversely across the body structure.

18. The method as in claim 1 further including maintaining a space between the electrode terminal and the body structure during the applying step.

19. The method of claim 1 wherein the electrically conductive fluid is directed through a cannula into a body cavity, the electrode terminal and the return electrode being submerged in the fluid within the body cavity.

20. The method of claim 1 further comprising providing one or more electrode terminals surrounded by an insulating matrix to electrically isolate each terminal, the insulating matrix comprising an inorganic material.

21. The method of claim 1 wherein the high frequency voltage is greater than 10 volts RMS and less than 1000 volts RMS.

22. The method of claim 1 wherein the electrode terminal is disposed over a lateral surface of an electrode support member.

23. The method of claim 1 wherein the electrode terminal has a shape selected from the group consisting essentially of flat, concave, convex, hemispherical, pyramidal, conical and cylindrical.

24. The method of claim 1 wherein the power to the electrode terminal is controlled based on the electrical impedance between the electrode terminal and the return electrode.

25. The method of claim 1 wherein temperature at the target site is measured by a temperature sensor adjacent to the electrode terminal such that power delivery to the electrode terminal is limited if the measured temperature exceeds a threshold value.

26. The method of claim 25 wherein the temperature sensor is integral with the electrode terminal.

* * * * *